United States Patent
Estay et al.

(10) Patent No.: US 11,982,661 B1
(45) Date of Patent: May 14, 2024

(54) SENSORY TRANSFORMER METHOD OF GENERATING INGREDIENTS AND FORMULAS

(71) Applicant: NotCo Delaware, LLC, Santiago (CL)

(72) Inventors: Alonso Vargas Estay, Santiago (CL); Hojin Kang, Santiago (CL); Francisco Clavero, Santiago (CL); Aadit Patel, Burlingame, CA (US); Karim Pichara, San Francisco, CA (US)

(73) Assignee: Notco Delaware, LLC, Santiago (CL)

( * ) Notice: Subject to any disclaimer, the term of this patent is extended or adjusted under 35 U.S.C. 154(b) by 0 days.

(21) Appl. No.: 18/203,431

(22) Filed: May 30, 2023

(51) Int. Cl.
    *G01N 33/02* (2006.01)
    *G06N 3/0455* (2023.01)

(52) U.S. Cl.
    CPC ........... *G01N 33/02* (2013.01); *G06N 3/0455* (2023.01)

(58) Field of Classification Search
    CPC .............................. G01N 33/02; G06N 3/0455
    See application file for complete search history.

(56) References Cited

U.S. PATENT DOCUMENTS

| | | | |
|---|---|---|---|
| 5,305,076 A | 4/1994 | Inoue et al. | |
| 8,044,354 B2 | 10/2011 | Werner et al. | |
| 8,419,433 B2 | 4/2013 | Do et al. | |
| 8,647,121 B1 * | 2/2014 | Witlin | G09B 19/0092 434/127 |
| 8,775,341 B1 | 7/2014 | Commons | |
| 9,015,093 B1 * | 4/2015 | Commons | G01C 21/3602 706/26 |

(Continued)

FOREIGN PATENT DOCUMENTS

| | | |
|---|---|---|
| CA | 3089817 A1 | 7/2019 |
| CN | 101793886 A | 8/2010 |

(Continued)

OTHER PUBLICATIONS

Fontanellaz, Matthias, Stergios Christodoulidis, and Stavroula Mougiakakou. "Self-attention and ingredient-attention based model for recipe retrieval from image queries." Proceedings of the 5th international workshop on multimedia assisted dietary management. 2019. (Year: 2019).*

(Continued)

*Primary Examiner* — Raymond L Nimox
(74) *Attorney, Agent, or Firm* — Haverstock & Owens, A Law Corporation

(57) ABSTRACT

Techniques to suggest one or more sets of ingredients that can be used to recreate or mimic a target sensory description using artificial intelligence are disclosed. An artificial intelligence model includes a transformer inspired neural network architecture that learns from ingredients, recipes, and sensory profiles. The artificial intelligence model includes a sensory transformer model that generates a probability distribution of source ingredients based on an embedding associated with first digital data representing ingredients and the second digital data representing sensory description, and a selector that selects at least one candidate ingredient from the probability distribution of source ingredients for the embedding. A complete set of ingredients generated based on the at least one candidate ingredient when combined become a food product that has or achieves the sensory description.

17 Claims, 12 Drawing Sheets

(56) References Cited

U.S. PATENT DOCUMENTS

| | | | |
|---|---|---|---|
| 9,053,431 B1* | 6/2015 | Commons | G06N 3/02 |
| 9,513,167 B2 | 12/2016 | Hargreaves et al. | |
| 9,519,620 B1 | 12/2016 | Pinel et al. | |
| 9,841,897 B2 | 12/2017 | Palmer et al. | |
| 10,325,181 B2 | 6/2019 | Xu et al. | |
| 10,515,715 B1 | 12/2019 | Pappas et al. | |
| 10,915,818 B1* | 2/2021 | Patel | G06N 3/045 |
| 10,957,424 B1 | 3/2021 | Navon et al. | |
| 10,962,473 B1 | 3/2021 | O'Hara et al. | |
| 10,970,621 B1 | 4/2021 | Pichara et al. | |
| 10,984,145 B1 | 4/2021 | Hutchinson et al. | |
| 10,993,465 B2* | 5/2021 | Pichara | G06F 40/30 |
| 11,048,976 B2 | 6/2021 | Tian et al. | |
| 11,164,069 B1 | 11/2021 | Korsunsky et al. | |
| 11,164,478 B2 | 11/2021 | Pichara et al. | |
| 11,205,101 B1 | 12/2021 | Garcia et al. | |
| 11,348,664 B1 | 5/2022 | Kaneko et al. | |
| 11,373,107 B1 | 6/2022 | Clavero et al. | |
| 11,404,144 B1 | 8/2022 | Kang et al. | |
| 11,514,350 B1 | 11/2022 | Kaneko et al. | |
| 2002/0184167 A1 | 12/2002 | McClanahan | |
| 2003/0157725 A1 | 8/2003 | Franzen et al. | |
| 2004/0153250 A1 | 8/2004 | Hurst et al. | |
| 2005/0143936 A1 | 6/2005 | Laughlin et al. | |
| 2007/0139667 A1 | 6/2007 | Russell et al. | |
| 2009/0055247 A1 | 2/2009 | Jackson | |
| 2011/0020518 A1 | 1/2011 | Delort et al. | |
| 2012/0082362 A1 | 4/2012 | Diem et al. | |
| 2012/0328178 A1 | 12/2012 | Remiszewski et al. | |
| 2013/0149679 A1 | 6/2013 | Tokuda et al. | |
| 2013/0221222 A1 | 8/2013 | Baiz et al. | |
| 2013/0222406 A1 | 8/2013 | Wolfe et al. | |
| 2014/0220217 A1 | 8/2014 | Brown et al. | |
| 2015/0199608 A1 | 7/2015 | Pinel et al. | |
| 2016/0025569 A1 | 1/2016 | Hargreaves et al. | |
| 2016/0110584 A1 | 4/2016 | Remiszewski et al. | |
| 2016/0358043 A1 | 12/2016 | Mu et al. | |
| 2017/0116517 A1* | 4/2017 | Chee | G06N 3/042 |
| 2017/0139902 A1 | 5/2017 | Byron et al. | |
| 2017/0220558 A1 | 8/2017 | Pinel et al. | |
| 2017/0238590 A1 | 8/2017 | Bansal-Mutalik et al. | |
| 2017/0345185 A1 | 11/2017 | Byron et al. | |
| 2018/0101784 A1 | 4/2018 | Rolfe et al. | |
| 2018/0192680 A1 | 7/2018 | Fraser et al. | |
| 2018/0203921 A1 | 7/2018 | Privault et al. | |
| 2018/0293489 A1 | 10/2018 | Eyster et al. | |
| 2018/0357299 A1 | 12/2018 | Miranda et al. | |
| 2019/0171707 A1 | 6/2019 | Rapaport | |
| 2019/0200797 A1 | 7/2019 | Diao et al. | |
| 2019/0228039 A1 | 7/2019 | Doble et al. | |
| 2019/0228855 A1 | 7/2019 | Leifer et al. | |
| 2019/0228856 A1* | 7/2019 | Leifer | G06F 16/9035 |
| 2019/0251441 A1 | 8/2019 | Lu et al. | |
| 2019/0295440 A1 | 9/2019 | Hadad | |
| 2020/0268032 A1 | 8/2020 | Okuyama et al. | |
| 2020/0309746 A1 | 10/2020 | Sakai | |
| 2020/0365053 A1 | 11/2020 | Pichara et al. | |
| 2021/0027379 A1 | 1/2021 | Zhu et al. | |
| 2021/0073944 A1 | 3/2021 | Liu et al. | |
| 2021/0141863 A1* | 5/2021 | Wu | G06N 3/08 |
| 2022/0012566 A1* | 1/2022 | Korsunsky | G06N 3/045 |
| 2022/0232863 A1 | 7/2022 | Sevgen | |
| 2022/0253447 A1* | 8/2022 | Boytsov | G06N 3/08 |

FOREIGN PATENT DOCUMENTS

| | | |
|---|---|---|
| CN | 105867634 A | 8/2016 |
| CN | 106663297 A | 5/2017 |
| CN | 106844738 A | 6/2017 |
| CN | 108509601 A | 4/2018 |
| CN | 108576832 A | 9/2018 |
| CN | 109219801 A | 1/2019 |
| CN | 110021404 A | 7/2019 |
| WO | 2004083451 A1 | 9/2004 |
| WO | 2013052824 A1 | 4/2013 |
| WO | 2016010097 A1 | 1/2016 |
| WO | 2017070605 A1 | 4/2017 |
| WO | 2020237214 A1 | 11/2020 |
| WO | 2021026083 A1 | 2/2021 |
| WO | 2021071756 A1 | 4/2021 |
| WO | 2022010503 A1 | 1/2022 |
| WO | 2022010544 A1 | 1/2022 |
| WO | 2022035464 A1 | 2/2022 |
| WO | 2022098381 A1 | 5/2022 |
| WO | 2022235326 A1 | 11/2022 |
| WO | 2022240439 A1 | 11/2022 |
| WO | 2022265698 A1 | 12/2022 |
| WO | 2023055569 A1 | 4/2023 |
| WO | 2023080922 A1 | 5/2023 |
| WO | 2023080923 A1 | 5/2023 |

OTHER PUBLICATIONS

W. A. d. Santos, J. R. Bezerra, L. F. Wanderley Góes and F. M. F. Ferreira, "Creative Culinary Recipe Generation Based on Statistical Language Models," in IEEE Access, vol. 8, pp. 146263-146283, 2020, doi: 10.1109/ACCESS.2020.3013436. (Year: 2020).*

Ma, Peihua, et al. "Vision-language models boost food composition compilation." arXiv preprint arXiv:2306.01747 (2023). (Year: 2023).*

Otter, Daniel W., Julian R. Medina, and Jugal K. Kalita. "A survey of the usages of deep learning for natural language processing." IEEE transactions on neural networks and learning systems 32.2 (2020): 604-624. (Year: 2020).*

Zou et al., "Regularization and Variable Selection via the Elastic Net", Department of Statistics, Stanford University, dated Dec. 5, 2003, 29 pages.

Bowman et al., "Generating Sentences from a Continuous Space", May 2016.

Rudinger et al., Skip-Prop: Representing Sentences with One Vector Pre Proposition, 12th International Conference on Computational Semantics, dated 2017, 7 pages.

Karamanolakis et al., "Item Recommendation with Variational Autoencoders and Heterogeneous Priors", DLRS, dated Oct. 2018, 5 pages.

Eating bird food, "Vegan "Chicken" Salad", https://www.eatingbirdfood.com/simple-vegan-mock-chicken-salad/, Apr. 5, 2017, downloaded Mar. 11, 2021. (Year: 2017).

Rong, Xin. word2vec Parameter Learning Explained. arXiv:1411.2738v4 [cs.CL] Jun. 5, 2016. (Year: 2016).

Salvador, Amaia, et al. "Learning cross-modal embeddings for cooking recipes and food images." Proceedings of the IEEE conference on computer vision and pattern recognition. 2017. (Year: 2017).

David Xu, "Machine Learning for Flavor Development," Bachelor's Thesis, Harvard College, School of Engineering and Applied Sciences, Apr. 5, 2019, 69 pages.

Hattab et al., Application of an Inverse Neural Network Model for the Identification of Optimal Amendment to Reduce Copper Toxicity in Phytoremediated Contaminated Soils, Journal of Geochemical Exploration, Elsevier, 2014, 136, pp. 14-23, 2014. (Year: 2014).

Kieaibi E., Determination of Protein Secondary Structure from Infrared Spectra Using Partial Least-Squares Regression, 9 pages, 2016 (Year: 2016).

Yang et al., "Obtaining information about protein secondary structures in aqueous solution using Fourier transform IR spectroscopy", Published online Feb. 5, 2015, nature protocols, 16 pages.

XGBoost, "Python Package Introduction", https://xgboost.readthedocs.io/en/latest/python/python_intro.html, last viewed on Nov. 5, 2020, 5 pages.

GitHub.com, "CMBI/DSSP", https://github.com/cmbi/dssp, last viewed on Nov. 5, 2020. 4 pages.

Wilcox et al., "Determination of Protein Secondary Structure from Infrared Spectra Using Partial Least-Squares Regression", dated 2016 American Chemical Society, 9 pages.

Sigma-Aldrich, "IR Spectrum Table and Chart", https://www.sigmaaldrich.com/technical-documents/articles/biology/ir-spectrum-table.html, last viewed on Nov. 5, 2020, 6 pages.

(56) References Cited

OTHER PUBLICATIONS

SciPy.org, "scipy.signal.savgol_filter", https://docs.scipy.org/doc/scipy/reference/generated/scipy.signal.savgol_filter.html, last viewed on Nov. 5, 2020, 3 pages.

SciPy.org, "scipy.integrate.simps", https://docs.scipy.org/doc/scipy/reference/generated/scipy.integrate.simps.html, last viewed on Nov. 5, 2020, 2 pages.

Scikitlearn.org, "sklearn.neighbors.KNeighborsRegressor", https://scikit-learn.org/stable/modules/generated/sklearn.neighbors.KNeighborsRegressor.html, last viewed on Nov. 5, 2020, 5 pages.

Scikitlearn.org, "sklearn.model_selection.GridSearchCV", https://scikit-learn.org/stable/modules/generated/sklearn.model_selection.GridSearchCV.html, last viewed on Nov. 5, 2020, 7 pages.

Scikitlearn.org, "sklearn.linear_model.lasso", https://scikit-learn.org/stable/modules/generated/sklearn.linear_model.Lasso.html, last viewed on Nov. 5, 2020, 6 pages.

Scikitlearn.org, "sklearn.cross_decomposition.PLSRegression", https://scikit-learn.org/stable/modules/generated/sklearn.cross_decomposition.PLSRegression.html , last viewed on Nov. 5, 2020, 5 pages.

Scikitlearn.org, "3.2.4.1.3. sklearn.linear_model.LassoCV", https://scikit-learn.org/stable/modules/generated/sklearn.linear_model.LassoCV.html, last viewed on Nov. 5, 2020, 6 pages.

ProDry, "DSSP Tools", http://prody.csb.pitt.edu/manual/reference/proteins/dssp.html, last viewed on Nov. 5, 2020, 2 pages.

Cao et al., "Optimization of Formulations Using Robotic Experiments Driven by Machine Learning DoE", Cell Reports Physical Science, Jan. 20, 2021, 17 pages.

Cromwell et al., "Computational Creativity in the Culinary Arts", Proceedings of the Twenty-Eighth International Florida Artificial Intelligence Research Society Conference, dated 2015, 5 pages.

Park et al., "FlavorGraph: a large-scale food-chemical grpah for generating food representations and recommending food pairings", Scientific Reports: nature Research, vol. 11, Jan. 13, 2021, 13 pages.

Yuan et al., "An Inductive Content-Augmented Network Embedding Model for Edge Artificial Intelligence", IEEE Transaction on Industrial Informatics, vol. 15 No. 7, Jul. 2019, pp. 4295-4305.

Hodgkin, "The Castlemaine Project: Development of an AI-based Drug Design Support System", Molecular Modelling and Drug Design, 1994, pp. 137-169.

Peiretti et al., "Artificial Intelligence: The Future for Organic Chemistry?", ACS Omega, 2018, 3 (10), pp. 13263-13266.

Fromm et al., "A Vector Space model for Neural Network Functions: Inspirations from Similarities between the Theory of Connectivity and the Logarithmic Time Course of Word Production", Frontiers in Systems Neuroscience, Aug. 28, 2020, 10 pages.

Hlahladakis et al., "An Overview of Chemical Additives Present in Plastics: Migration, Release, Fate and Environmental Impact During Their Use, Disposal and Recycling", Journal of Hazardous Materials 344 (2018), pp. 179-199.

Paul, Rahl, "Classifying Cooking Object's State using a Tuned VGG Convolutional Neural Netwrok," May 2018, 5 pages.

De Clercq et al., "Data-Driven Recipe Completion Using Machine Learning Methods," Trends in Food Science & Technology 49 (2016), Dec. 2015, p. 1-13.

Pinel et al., Chapter 16: A Culinary Computational Creativity System, Computational Creativity Research: Towards Creative Machines, Jan. 2014, pp. 327-346.

springwise.com, "Artificial Intelligence Uses Algorithms To Make Nutritious Vegan Meat," https://www.springwise.com/artificial-intelligence-algorithms-vegan-meat/, last viewed May 5, 2023, 2 pages.

Malav et al., "Meat analogue: A Review, Critical Reviews in Food Science and Nutrition," DOI: 10.1080/10408398.2012.689381, 2013, 16 pages.

pbc.com, "Could AI help to create a meat-free world?", https://www.bbc.com/future/article/20171214-could-ai-help-create-a-meat-free-world, last viewed May 5, 2023, 7 pages.

Silva et al, "An expert system for automated flavour matching—Prioritizer", DOI: 10.1002/ffj.3386, 2017, 8 pages.

Severcan et al., "Estimation of protein secondary structure from FTIR spectra using neural networks", Journal of Molecular Structure 565-566 (2001) 383-397, 5 pages.

Hering et al., "An alternative method for rapid quantification of protein secondary structure from FTIR spectra using neural networks", Spectroscopy 16 (2002) 53-69, 18 pages.

Akkas et al., "Effects of lipoic acid supplementation on rat brain tissue: An FTIR spectroscopic and neural network study", Food Chemistry 105 (2007) 1281-1288, DOI:10.1016/j.foodchem.2007/03.015, 8 pages.

Yin et al., "A Multi-view generative model for molecular representation improves prediction tasks", Dec. 22, 2020 (Dec. 22, 2020), XP093054731, https://math.mit.edu/research/highschool/primes/materials/2020/Yin-Chung-Regev.pdf, last viewed Jun. 26, 2023, 6 pages.

Chuang et al., "Learning Molecular Representations for Medicinal Chemistry", J. Med. Chem., vol. 63 No. 16, May 4, 2020 (May 4, 2020), pp. 8705-8722, XP093054503, US ISSN: 0022-2623, DOI: 10.1021/acs.jmedchem.0C00385, https://pubs.acs.org/doi/pdf/10.1021/acs.jmedchem.0c00385, last viewed Jun. 26, 2023.

Finlayson et al., "Cross-modal representation alignment of molecular structure and perturbation-induced transcriptional profiles", arxiv.org, Cornell University Library, 201 Olin Library Cornell Univeristy Ithaca, NY 14853, Oct. 2, 2020 (Oct. 2, 2020), XP081776101, 17 pages.

Sanchez-Lengeling et al., "Machine Learning for Scent: Learning Generalizable Perceptual Representations of Small Molecules", arxiv.org, Cornell University Library, 201 Olin Library Cornell University Ithaca, NY 14853, Oct. 23, 2019 (Oct. 23, 2019), XP081519777, 18 pages.

Cai et al., "Molecular Similarity: Methods and Performance", Chinese Journal of Chemistry, Zhongguo Kexueyuan, CN, vol. 31, No. 9, Sep. 16, 2013 (Sep. 16, 2013), pp. 1123-1132, XP071929110, ISSN: 1001-604X, DOI: 10.1002/CJOC.201300390.

Druck, "Recipe Attribute Prediction using Review Text as Supervision", Cooking with Computers 2023, IJCAI workshop, Jan. 1, 2023 (Jan. 1, 2013), XP093046521, Retrieved from the Internet: URL:https://projet.liris.cnrs.fr/cwc/papers/cwc2013_submission_6.pdf [retrieved on May 12, 2023], 9 pages.

Howell-phowell et al., "Analyzing Taste Preferences from Crowdsourced Food Entries", Digital Health Conference, ACM, 2 Penn Plaza, Suite 701, New York NY 10121-0701 USA, Apr. 11, 2016 (Apr. 11, 2016), pp. 131-140, XP058081473, DOI: 10.1145/2896338.2896358, ISBN: 978-1-4503-4224-7.

Ermi et al., "Deep Learning Approaches to Chemical Property Prediction from Brewing Recipes", 2018 International Joint Conference of Neural Networks (IJCNN), IEEE, Jul. 8, 2018 (Jul. 8, 2018), pp. 1-7, XP033419345, DOI: 10.1109/IJCNN.2018.8489492 [retrieved on Oct. 10, 2018].

Baruque et al., "Hybrid Classification Ensemble Using Topology-preserving Clustering", New Generation Computing, Verlag Omsha Tokio, Heidelberg, vol. 29 No. 3, Aug. 4, 2011 (Aug. 4, 2011), pp. 329-344, XP019941484, ISSN: 1882-7055, DOI: 10.1007/S00354-011-0306-X.

Natarajan et al., "Optimal Classification with Multivariate Losses", Proceedings of the 33rd International Conference on Machine Learning, New York, NY, USA, 2016. JMLR: W&CP vol. 48, 9 pages. (Year: 2016).

Theodoridis et al., "Cross-modal Variational Alignment of Latent Space", 2020 IEEE/CVF Conference on Computer Vision and Pattern Recognition Workshops, Jun. 2020, DOI:10.1109/CVPRW50498.2020.00488, 10 pages.

Theodoridis et al., "A Cross-Modal variational Framework for Food Image Analysis", Proceedings / ICIP, International Conference on Image Processing, Jun. 2020, DOI:10.1109/ICIP40778.2020.9190758, 5 pages.

Salvador et al., "Inverse Cooking: Recipe Generation from Food Images", 2019 IEEE/CVF Conference on Computer Vision and Pattern Recognition (CVPR), Jun. 2019, DOI:10.1109/CVPR.2019.01070, 24 pages.

(56) References Cited

OTHER PUBLICATIONS

Shirai et al., "Identifying Ingredient Substitutions Using a Knowledge Graph of Food", Frontiers in Artificial Intelligence, vol. 3, Jan. 25, 2021 (Jan. 25, 2021), XP093076438, DOI: 10.3389/frai.2020.621766, 10 pages.

Pellegrini et al., "Exploiting Food Embeddings for Ingredient Substitution", Proceedings of the 14th International Joint Conference on Biomedical Engineering Systems and Technologies, Feb. 11-13, 2021, vol. 5, Feb. 2021 (Feb. 2021), pp. 67-77, XP093077170, DOI: 10.5220/0010202000670077, ISBN: 978-989-758-490-9, 11 pages.

Teng et al., "Recipe recommendation using ingredient network", Arxiv.org, Cornell University Library, 201 Olin Library Cornell University Ithaca, NY 14853, Nov. 16, 2011 (Nov. 16, 2011), XP080539899, DOI: 10.1145/2380718.2380757, 10 pages.

\* cited by examiner

SENSORY TRANSFORMER METHOD OF GENERATING INGREDIENTS AND FORMULAS

TECHNICAL FIELD

One technical field of the present disclosure is artificial intelligence and machine learning, as applied to food. Another technical field is food science. The disclosure relates, in particular, to use of machine learning to generate food ingredients and food formulas for foods based on sensory data.

BACKGROUND

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Today, many negative consequences of use of animals in the food industry are known, such as deforestation, pollution, human health conditions, and allergies, among others. In contrast, a plant-based diet is associated with improved health and well-being and reduces risk of diseases. Not only is a plant-based diet good for our health but it is also good for the Earth's health. Research has shown that production of plant-based food items generates less greenhouse emissions and require less energy, water, and land than production of animal-based food items. There are plant alternatives to animal-based food items. For example, plant alternatives to meat include veggie burgers and other vegan meat food items. However, these alternatives do not match the taste and texture of meat.

Accordingly, there is a need for improved techniques to mimic a target food item, such as an animal-based target food item, by matching nutritional and sensory attributes as much as possible. Unfortunately, many techniques for development of new foods rely upon time-consuming, inaccurate, manual laboratory work in which different ingredients are combined in different ways and tested. These approaches are inefficient, involve extensive time to develop a single successful food formula, and waste physical resources.

SUMMARY

The appended claims may serve as a summary of the invention.

BRIEF DESCRIPTION OF THE FIGURES

The present invention is illustrated by way of example, and not by way of limitation, in the figures of the accompanying drawings and in which like reference numerals refer to similar elements and in which.

DETAILED DESCRIPTION

Figure 1:
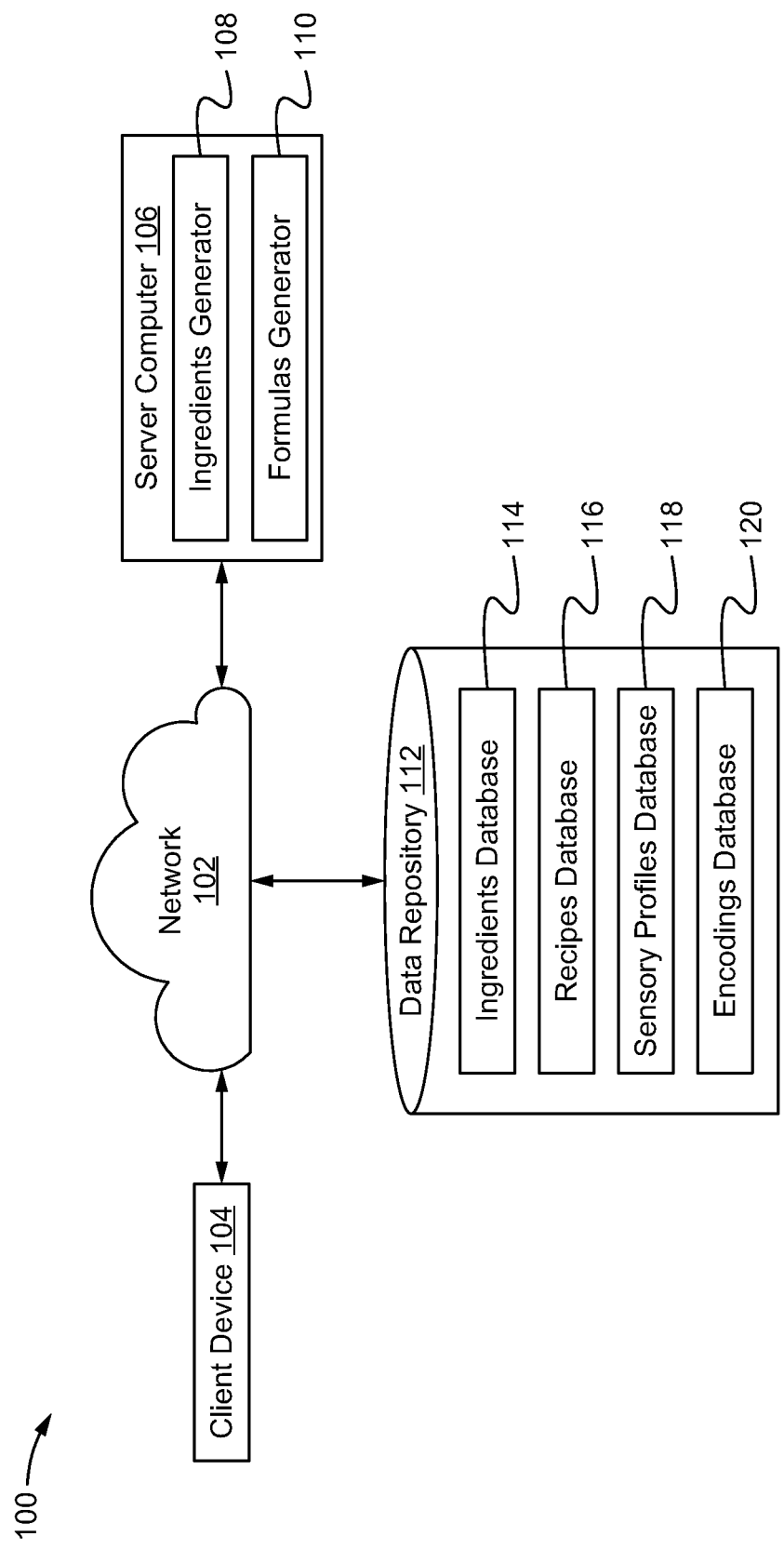
FIG. 1 illustrates an example networked computer system with which various embodiments may be practiced.

In the following description, for the purposes of explanation, numerous specific details are set forth in order to provide a thorough understanding of the present invention. It will be apparent, however, that the present invention may be practiced without these specific details. In other instances, well-known structures and devices are shown in block diagram form in order to avoid unnecessarily obscuring the present invention.

Embodiments are described herein in sections according to the following outline:

1.0 GENERAL OVERVIEW
2.0 STRUCTURAL OVERVIEW
3.0 FUNCTIONAL OVERVIEW
   3.1 INGREDIENTS GENERATOR
      3.1.1 SENSORY TRANSFORMER MODEL
         3.1.1.1 NEURAL NETWORK LANGUAGE-BASED MODELS
         3.1.1.2 NEURAL ATTENTION-BASED MODEL
      3.1.2 SELECTOR
   3.2 FORMULA GENERATOR
      3.2.1 SENSORY TRANSFORMER MODEL
      3.2.2 SELECTOR
4.0 EXAMPLE RECOMMENDATIONS
5.0 PROCEDURAL OVERVIEW
6.0 HARDWARE OVERVIEW
7.0 SOFTWARE OVERVIEW
8.0 OTHER ASPECTS OF DISCLOSURE

1.0 GENERAL OVERVIEW

Computer-implement techniques for generating candidate ingredients and candidate formulas that can be used to create a food product that mimics (resembles, similar to) or has a target sensory description using artificial intelligence are disclosed.

In some embodiments, an artificial intelligence model includes a transformer inspired neural network architecture that learns from a repository including at least an ingredients database, recipes database, and sensory profiles database. The artificial intelligence model learns insights from ingredient names, roles they play in recipe formulas, and sensorial descriptions associated with those formulas. The artificial intelligence model generates sets of ingredients that combined become a food product with a specific sensory profile.

One objective of the artificial intelligence model is to take a target sensory profile and an optional base formula to obtain a set of ingredients that could match or otherwise mimic the target sensory profile. Another objective of the artificial intelligence model is to learn sensory embeddings for each ingredient using sensory data from chef reviews (human sensory feedback).

In an embodiment, a computer-implemented method of suggesting candidate ingredients comprises applying an artificial intelligence model to first digital data representing ingredients and second digital data representing sensory description. The artificial intelligence model comprises a sensory transformer model that generates a probability distribution of source ingredients based on an embedding associated with first digital data representing ingredients and the second digital data representing sensory description, and a selector that selects at least one candidate ingredient from the probability distribution of source ingredients for the embedding. The method also comprises, in response to applying the artificial intelligence model, identifying the at least one candidate ingredient, wherein when ingredients in a complete set of ingredients generated based on the at least one candidate ingredient are combined to become a food product that has or achieves the sensory description.

In an embodiment, the sensory transformer model includes an encoder including a first neural network language-based model and a second neural network language-based model, and a decoder including a neural attention-based model. The first digital data may be obtained by applying the first neural network language-based model to names of the ingredients, and the second digital data may be obtained by applying the second neural network language-based model to the sensory description.

In an embodiment, the first neural network language-based model comprises a language model and a dense layer, wherein [CLS] token representations generated by the language model and the second digital data are used to train the dense layer. The dense layer represents the ingredients in a new space that contains sensory data.

In an embodiment, the neural attention-based model comprises a plurality of attention layers and a classification layer. The embedding may be generated by applying the plurality of attention layers to the first digital data representing ingredients and the second digital data representing sensory description. The probability distribution of source ingredients may be generated by the classification layer for the embedding.

All embodiments disclosed and claimed herein are directed to a computer-implemented programmed processes that interact with digital data to provide a practical application of computing technology to the problem of generating sets of ingredients that when combined become a food product with specific functional (e.g., sensorial) properties. The disclosure is not intended to encompass techniques for organizing human activity, for performing mental processes, or for performing a mathematical concept, and any interpretation of the claims to encompass such techniques would be unreasonable based upon the disclosure as a whole.

Other embodiments, aspects, and features will become apparent from the reminder of the disclosure as a whole.

2.0 STRUCTURAL OVERVIEW

FIG. 1 illustrates an example networked computer system 100 with which various embodiments may be practiced.

FIG. 1 is shown in simplified, schematic format for purposes of illustrating a clear example and other embodiments may include more, fewer, or different elements. FIG. 1, and the other drawing figures and all of the description and claims in this disclosure, are intended to present, disclose and claim a technical system and technical methods comprising specially programmed computers, using a special-purpose distributed computer system design and instructions that are programmed to execute the functions that are described. These elements execute functions that have not been available before to provide a practical application of computing technology to the problem of generating ingredients and formulas for plant-based foods. In this manner, the disclosure presents a technical solution to a technical problem, and any interpretation of the disclosure or claims to cover any judicial exception to patent eligibility, such as an abstract idea, mental process, method of organizing human activity or mathematical algorithm, has no support in this disclosure and is erroneous.

In some embodiments, the networked computer system comprises a client device(s) 104, a server computer 106, a data repository(ies) 112, which are communicatively coupled directly or indirectly via one or more networks 102.

The server computer 106 utilizes a set of one or more computer programs or sequences of program instructions that implement machine learning algorithms to generate candidate ingredients and candidate formulas such that each candidate formula along with a base formula, if any, result in a complete formula that has a sensory profile that mimics a given target sensory profile. Programs or sequences of instructions organized to implement the ingredient generating functions in this manner may be referred to herein as an ingredients generator 108. Programs or sequences of instructions organized to implement the formula generating functions in this manner may be referred to herein as a formulas generator 110. In an embodiment, the server computer 106 broadly represents one or more computers, such as one or more desktop computers, server computers, a server farm, a cloud computing platform (like Amazon EC2, Google Cloud, container orchestration (Kubernetes, Docker, etc.), or a parallel computer, virtual computing instances in public or private datacenters, and/or instances of a server-based application.

Each of the ingredients generator 108 and the formulas generator 110 includes a sensory transformer model and a selector. Components of the ingredients generator 108 and the formulas generator 110 may be implemented using software, hardware, firmware, or a combination thereof. In one embodiment, one or more of the components comprise one or more sequences of computer program instructions that are programmed to execute the functions that are described herein for the foregoing elements. In an embodiment, one or more of the components may include a processor configured to execute instructions stored in a non-transitory computer readable medium.

In an embodiment, the ingredients generator 108 is programmed to generate encoded representation of a plurality of ingredients that represent sensory features (generally, functional properties), and to predict candidate ingredients for a target (specific, desired) sensory description.

In an embodiment, the formulas generator 110 is programmed to predict candidate formulas based on candidate ingredients predicted by the ingredients generator 108 for a target sensory description. Each candidate formula along with base ingredients, if any, becomes a complete food formula such that a corresponding food product has or otherwise achieves the target sensory description. Base ingredients collectively together may be referred to herein as a base formula.

In some embodiments, in keeping with sound software engineering principles of modularity and separation of function, the ingredients generator 108 and the formulas generator 110 are implemented as a logically separate program, process or library.

The server computer 106 also includes receiving instructions (not illustrated) and displaying instructions (not illustrated). The receiving instructions are programmed to receive data from a client device 104 and/or a data repository 112 for further processing. For example, the receiving instructions may be programmed for receiving user input, such as user input identifying or specifying ingredient names, sensory descriptions, etc. The displaying instructions are programmed to cause one or more computing devices, such as a client device 104 to display a graphical user interface (GUI) including content, such as content from data repository 112 and/or generated by the ingredients generator 108 and/or the formulas generator 110. Other sets of instructions may be included to form a complete system such as an operating system, utility libraries, a presentation layer, database interface layer and so forth.

Computer executable instructions described herein may be in machine executable code in the instruction set of a CPU and may have been compiled based upon source code written in Python, JAVA, C, C++, OBJECTIVE-C, or any other human-readable programming language or environment, alone or in combination with scripts in JAVASCRIPT, other scripting languages and other programming source text. In another embodiment, the programmed instructions also may represent one or more files or projects of source code that are digitally stored in a mass storage device such as non-volatile RAM or disk storage, in the systems of FIG. 1 or a separate repository system, which when compiled or interpreted cause generating executable instructions which when executed cause the computer to perform the functions or operations that are described herein with reference to those instructions. In other words, the figure may represent the manner in which programmers or software developers organize and arrange source code for later compilation into an executable, or interpretation into bytecode or the equivalent, for execution by the formula generator 114.

The server computer 106 may be coupled (directly or indirectly) to the data repository 112 that includes an ingredients database 114, a recipes database 116, a sensory profiles database 118, and an encodings database 120.

The ingredients database 114 includes raw plant-based ingredients from various sources, such as from USDA's National Agricultural Library. Some non-limiting examples of plant-based ingredients may include vegetables (e.g., onions, potatoes, garlic, spinach, carrots, celery, squash, etc.), fruits (e.g., apples, pears, grapes, etc.), herbs (e.g., oregano, cilantro, basil, etc.), spices (e.g., black peppers, turmeric, red chili peppers, cinnamon, etc.), oils (e.g., corn oil, olive oil, etc.), nuts (e.g., almonds, walnuts, pistachios, etc.), legumes (e.g., lentils, dried peas, soybeans, etc.), starch, proteins, fibers, carbohydrates, sugar, etc. However, in some embodiments, the ingredients database 114 also includes ingredients that are animal-based, water-based, synthetic, or a combination thereof. Some non-limiting examples of animal-based ingredients may include dairy products (e.g., milk, butter, cheese, yogurt, ice cream, etc.), egg-based products (e.g., mayonnaise, salad dressings, etc.), meat products (e.g., burger patties, sausages, hot dogs, bacon, etc.), and/or seafood (e.g., fish, crab, lobsters, etc.).

Synthetic ingredients may include artificially produced food, e.g., artificial meats, artificial sweeteners, artificial milk, etc. The ingredients in the ingredients database 114 are referred to as source ingredients.

The recipes database 116 includes recipe formulas, each having one or more ingredients from the ingredients database 114. Each recipe formula in the recipe database 116 may include raw text. As an example, each recipe formula in the recipe database 116 may specify a name of each ingredient (e.g., lemon juice, avocado, onion, cilantro, etc.) in the recipe formula. Each recipe formula in the recipes database 116 may also include functional properties of the cooked or otherwise prepared food dish associated with the recipe formula. The functional properties may include human sensory feedback such as taste (e.g., salt, sweet, bitter, sour, and umami), texture descriptors, acceptance, and the like, which may be stored with the recipe formulas in the recipe database 116 or separately from the recipe formulas in the sensory profiles database 118 or another database of the data repository 112.

The sensory profiles database 118 includes a sensory profile of each recipe formula in the recipe database 116. The sensory profile of a recipe formula includes at least a sensory description corresponding to human sensory feedback for the recipe formula. For example, a sensory profile may include a sensory description such as "creamy texture and sweet flavor" or "sweet cocoa flavor with creamy texture." In some embodiments, a training set including at least a portion of the recipe formulas and their corresponding sensory profiles, is used to train various models described herein such as neural network language-based models and neural attention-based model.

The encodings database 120 includes ingredient vector representations, ingredient embeddings, and sensory vector representations (e.g., those generated by the ingredients generator 108 and the formulas generator 110). Generally, a vector representation is a token embedding that contains information about every other token in a sequence of tokens. Each ingredient in a recipe formula is associated with an ingredient vector representation. Similarly, each sensory property of a recipe formula is associated with a sensory vector representation. An ingredient embedding of an ingredient is a representation in an encoded space that contains sensory properties. Each ingredient in a recipe formula is associated with an ingredient embedding that contains sensory properties of the recipe formula. The encodings database 120 may also include other representations generated by the ingredients generator 108 and/or the formulas generator 110 during training and/or inference.

The data repository 112 may include other databases storing proprietary data relating to each source ingredient in the ingredients database 114, to each recipe formula in the recipes database 116, and other information that may be used by the ingredients generator 108 and formulas generator 110. Each database 114, 116, 118, 120 may be implemented using memory, e.g., RAM, EEPROM, flash memory, hard disk drives, optical disc drives, solid state memory, or any type of memory suitable for database storage.

The network 102 broadly represents a combination of one or more local area networks (LANs), wide area networks (WANs), metropolitan area networks (MANs), global interconnected internetworks, such as the public internet, or a combination thereof. Each such network may use or execute stored programs that implement internetworking protocols according to standards such as the Open Systems Interconnect (OSI) multi-layer networking model, including but not limited to Transmission Control Protocol (TCP) or User Datagram Protocol (UDP), Internet Protocol (IP), Hypertext Transfer Protocol (HTTP), and so forth. All computers described herein may be configured to connect to the network 102 and the disclosure presumes that all elements of FIG. 1 are communicatively coupled via the network 102. The various elements depicted in FIG. 1 may also communicate with each other via direct communications links that are not depicted in FIG. 1 for purposes of explanation.

The ingredients generator 108 and the formulas generator 110 (and, more generally, the server computer 106) are accessible over the network 102 by multiple computing devices, such as a client device 104, to request candidate ingredients or candidate formulas based on a target sensory description and an optional base formula including base ingredients. The client device 104 may comprise a desktop computer, laptop computer, tablet computer, smartphone, or any other type of computing device that allows access to the server computer 106. The elements in FIG. 1 are intended to represent one workable embodiment but are not intended to constrain or limit the number of elements that could be used in other embodiments.

3.0 FUNCTIONAL OVERVIEW

In an embodiment, the ingredients generator 108 and the formulas generator 110 interoperate programmatically in an unconventional manner to generate (determine, predict) one or more candidate ingredients and one or more candidate formulas, for a target sensory description. A candidate formula, predicted based on the one or more candidate ingredients, when combined (cooked, prepared) with one or more base ingredients, if previously (initially, originally) identified, become a food product having or achieving the target sensory description. One or more candidate ingredients, one or more candidate formulas, and/or one or more complete formulas may be displayed on the client device 104 (e.g., in a graphical user interface of the client device 104). It is noted that a complete formula is a formula that includes a base formula, if any, and a candidate formula.

In an embodiment, one or more complete formulas, may be transmitted downstream to a recipes generator for further processing such as to determine a new recipe including a set of cooking directions or instructions for that formula. An example recipes generator is described in co-pending U.S. patent application Ser. No. 17/479,770, filed Sep. 20, 2021, titled "Systems and Methods to Mimic Target Good Items using Artificial Intelligence," wherein the entire contents of which are hereby incorporated by reference as if fully set forth herein. A food product may be cooked (prepared, combined) according to the set of cooking directions or instructions for that complete formula.

3.1 Ingredients Generator

The ingredients generator 108 of FIG. 1 includes a sensory transformer model and a selector.

3.1.1 Sensory Transformer Model

Figure 2:
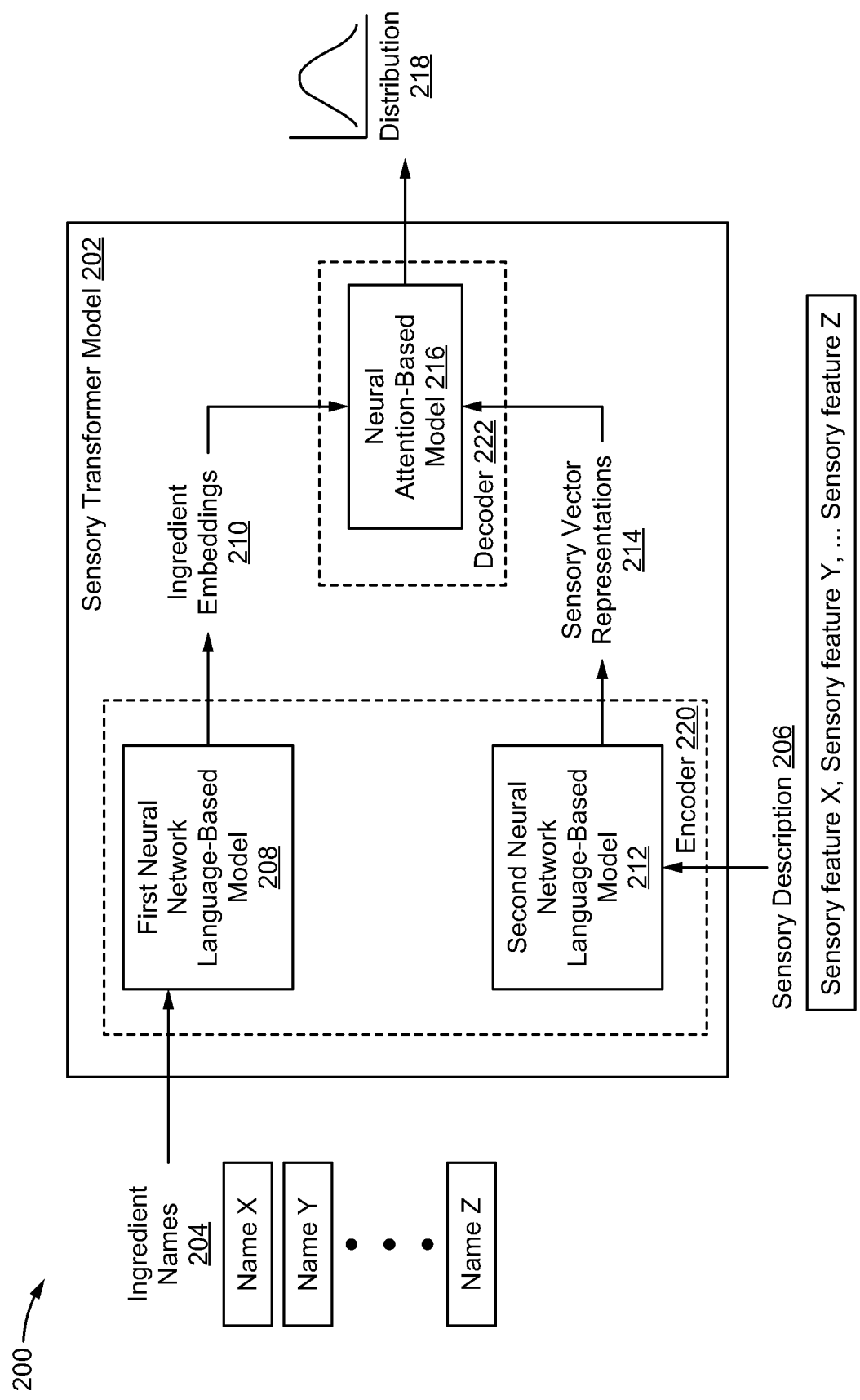
FIG. 2 illustrates a block diagram of an example sensory transformer model in accordance with some embodiments.

FIG. 2 illustrates a block diagram 200 of an example sensory transformer model in accordance with some embodiments.

A sensory transformer model 202 of FIG. 2 receives names of ingredients 204, such as base ingredients from a recipe formula, and a corresponding sensory description 206, such as from a sensory profile of the recipe formula, as inputs to the sensory transformer model 202. (As further discussed below, during inference, base ingredients are optional inputs to the ingredients generator 108 and, by extension, to the sensory transformer model of the ingredients generator 108.) The sensory transformer model 202 determines (generates) a probability distribution 218 of all possible ingredients (e.g., all source ingredients in the ingredients database 114) as an output that is used by a downstream selector to output one or more candidate ingredients that may be used to improve the recipe formula. It is noted that the sum of all probabilities determined for all ingredients in the probability distribution 218 is one.

The sensory transformer model 202 includes a first neural network language-based model 208, a second neural network language-based model 212, and a neural attention-based model 216. The first neural network language-based model 208 and the second neural network language-based model 212 are configured as an encoder 220 of the sensory transformer model 202. The neural attention-based model 216 is configured as a decoder 222 of the sensory transformer model 202.

3.1.1.1 Neural Network Language-Based Models

The encoder 220 of the sensory transformer model 202 includes the first neural network language-based model 208 and the second neural network language-based model 212, as shown in FIG. 2.

Figure 3:
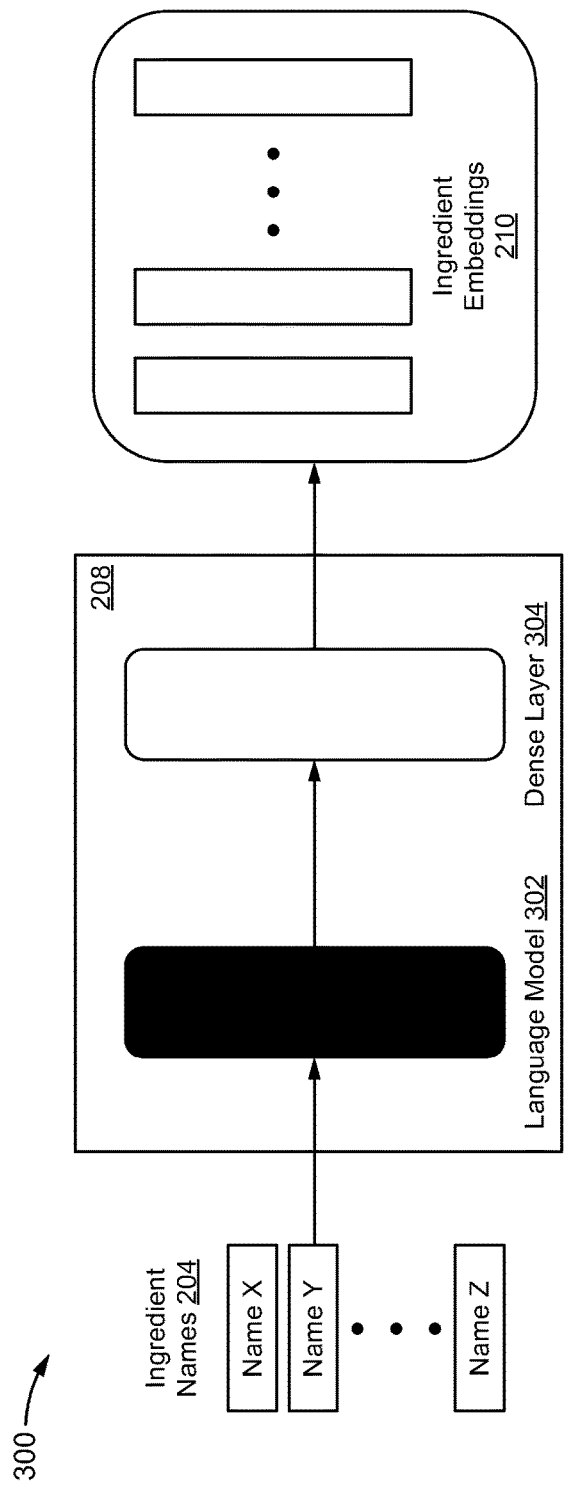
FIG. 3 illustrates a block diagram of an example first neural network language-based model in accordance with some embodiments.

A block diagram 300 of the first neural network language-based model 208 of the sensory transformer model 202 is illustrated in FIG. 3, in accordance with some embodiments.

The first neural network language-based model 208 receives names of ingredients, such as ingredient names 204, as inputs and determines (generates) ingredient embeddings 210 for corresponding ingredients as outputs. The ingredient embeddings 210 may be stored in the encodings database 120.

The first neural network language-based model 208 includes a language model 302 and a dense layer 304. An example language model 302 may be the BERT (Bidirectional Encoder Representations from Transformers) language model. Other language models, such as RoBERTa, XLNet, DistilBERT, ALBERT, T5, GPT-3, LaMDA, are contemplated. The language model 302 may be a pre-trained model that had already been trained in another dataset and with another task. In an embodiment, the language model 208 is not fine-tuned (retrained) and is static.

Names of ingredients represented initially in their own ingredient names are each input into the first neural network language-based model 208. This allows the first neural network language-based model 208 to recognize any ingredient that can be used in a formula to be contemplated. The language model 302 uses tokens to represent an input (e.g., an ingredient name). A [CLS] token (also referred to herein as [CLS] token representation) is a special token that is used to represent the entire input sequence. For example, a [CLS] token generated by the language model 302 represents an ingredient name with a single embedding. The [CLS] token is generated for classification purposes. The language model 302 also generates ingredient vector representations of input ingredient names from the [CLS] tokens corresponding with those ingredient names. Each ingredient vector representation of a corresponding ingredient represents relationship of the ingredients input to the first neural network language-based model 208. The ingredient vector representations may be stored in the encodings database 120.

Unlike the language model 302, the dense layer 304 is trained with the rest of the sensory transformer model 202. The dense layer 304 may be trained using [CLS] tokens (classification tokens) generated by the language model 302.

The dense layer 304 projects the ingredient vector representations in an encoded space that contains sensory data, transforming the ingredient vector representations into ingredient embeddings that contain sensory features. The ingredient embeddings 210 are inputs to the downstream neural attention-based model 216. In some embodiments, these ingredient embeddings 210 may also be externalized to other tasks.

Figure 4:
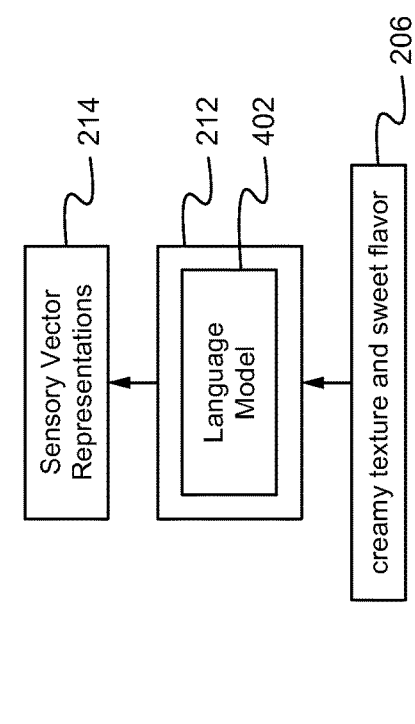
FIG. 4 illustrates a block diagram of an example second neural network language-based model in accordance with some embodiments.

A block diagram 400 of the second neural network language-based model 212 of the sensory transformer model 202 is illustrated in FIG. 4, in accordance with some embodiments.

The second neural network language-based model 212 receives a sensory description, such as from sensory description 206, as an input and generates sensory vector representations 214 for all described sensory properties as outputs. The sensory vector representations may be stored in the encodings database 120.

The second neural network language-based model 212 includes a language model 402. The language model 402 may be the same instance as the language model 302. Alternatively, the language model 402 is a different instance from the language model 302. The language model 402 generates sensory vector representations of sensory properties, such as "creamy texture," "sweet flavor," and the like. The sensory vector representations 214 are inputs to the downstream neural attention-based model 216. In addition, the sensory vector representations 214 are used to train the dense layer 304. In an embodiment, the language model 402 utilizes every token associated with a sensory description, such as the sensory description 206, except for special tokens such as [CLS] and [EOS] tokens.

3.1.1.2 Neural Attention-Based Model

The decoder 222 of the sensory transformer model 202 includes the neural attention-based model 216, as shown in FIG. 2. Given sensory vector representations 214 and ingredient embeddings 210, the neural attention-based model 216 determines which candidate ingredient(s) to use as a basis for complete formulas so that the sensory profile can be reached (achieved, obtained).

Figure 5A:
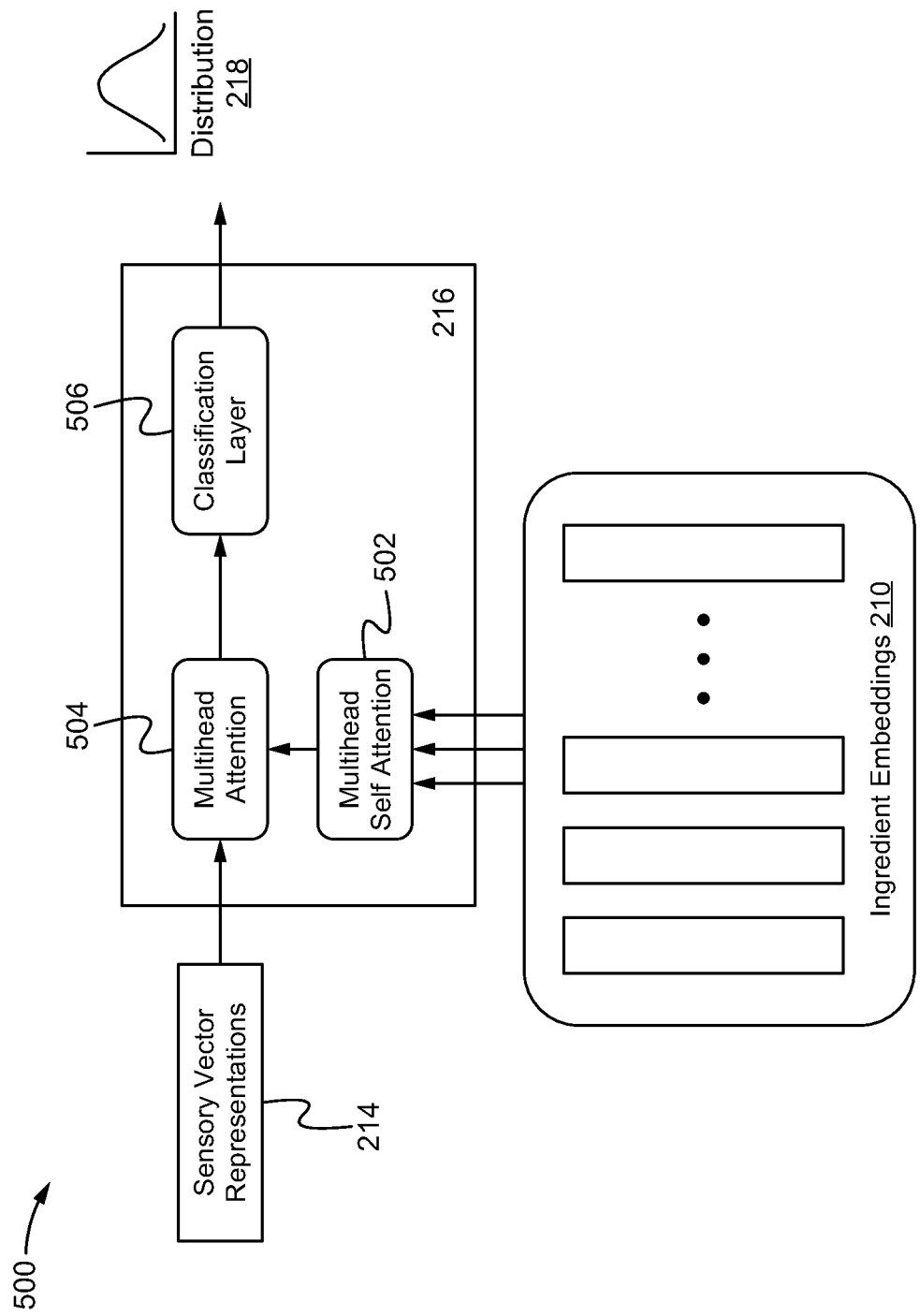
FIG. 5A illustrates a block diagram of an example neural attention-based model in accordance with some embodiments.

A block diagram 500 of the neural attention-based model 216 of the sensory transformer model 202 is illustrated in FIG. 5A, in accordance with some embodiments.

The neural attention-based model 216 receives ingredient embeddings 210 (from the first neural network language-based model 208) and sensory vector representations 214 (from the second neural network language-based model 212), as inputs and generates (determines, predicts, selects) the probability distribution 218 of all possible ingredients (e.g., all source ingredients in the ingredients database 114) given the inputs to the neural attention-based model 216.

The neural attention-based model 216 includes a self-attention layer 502, an attention layer 504, and a classification layer 506. These attention layers 502, 504 learn contextual information from ingredient embeddings and then from sensory vector representations. For example, the self-attention layer 502 and the attention layer 504 are adapted to receive the ingredient embeddings 210 and the sensory vector representations 214 as inputs to the neural attention-based model 216.

Figure 5B:
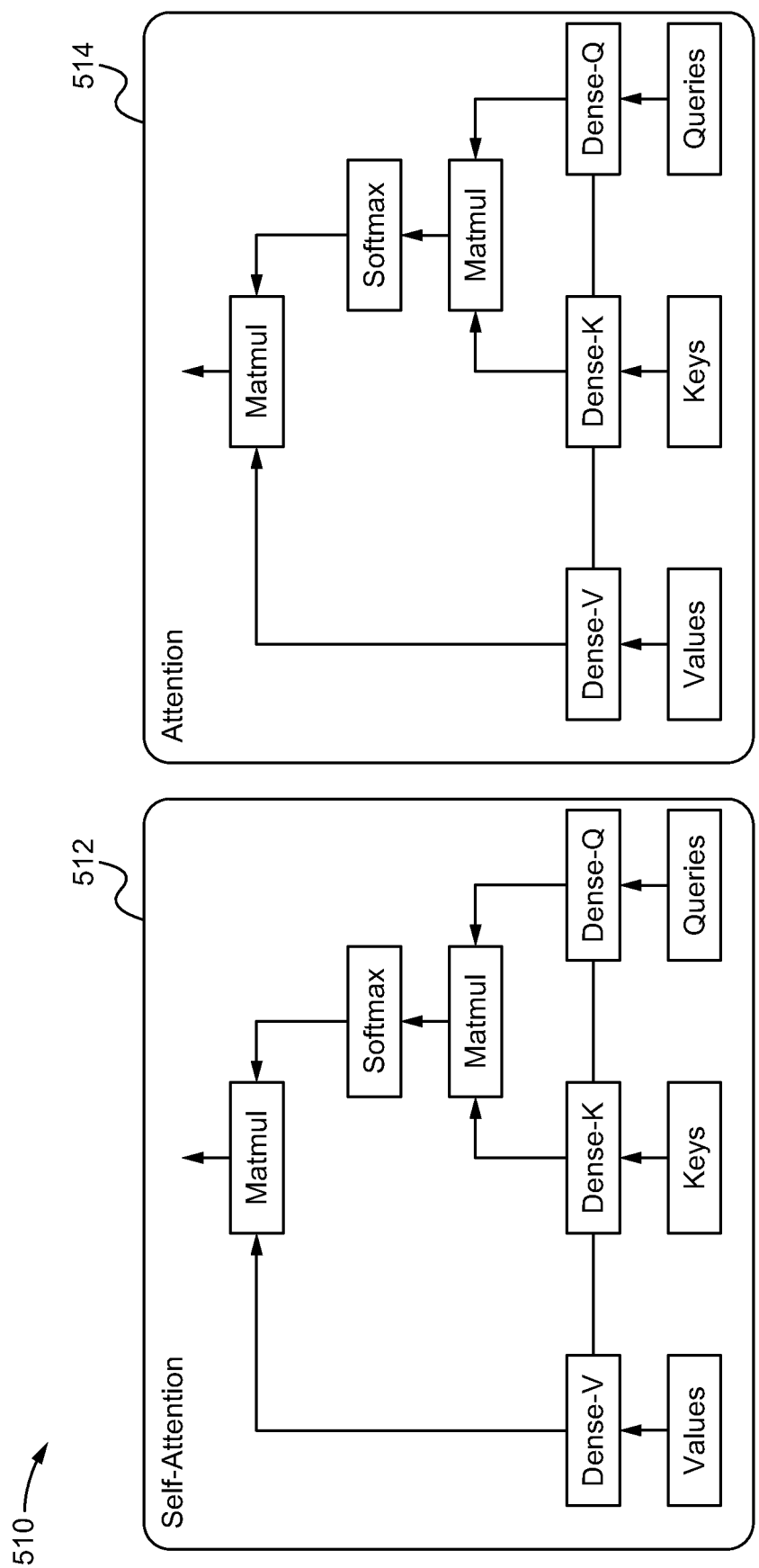
FIG. 5B illustrates a block diagram of prior attention mechanisms.
Figure 5C:
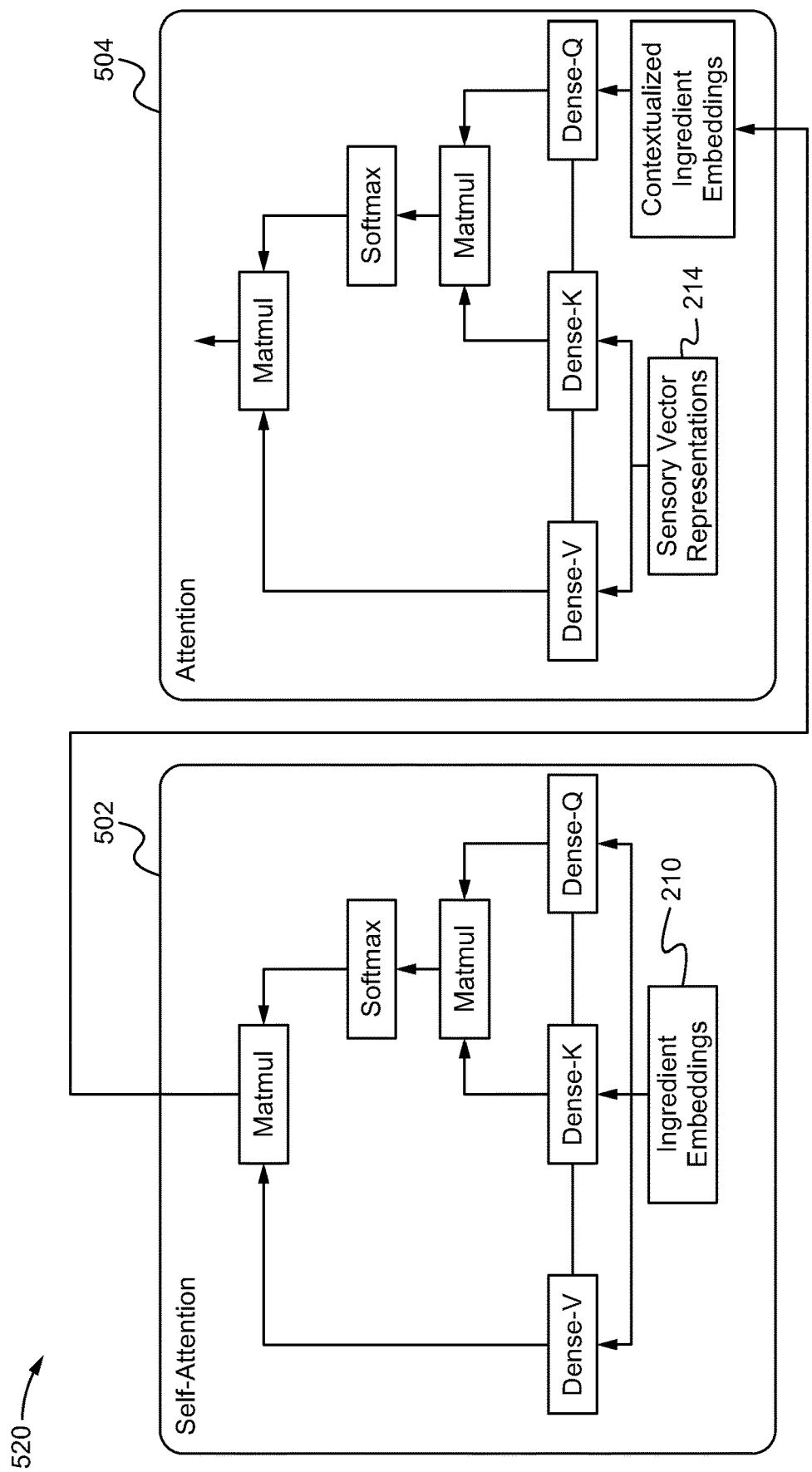
FIG. 5C illustrates a block diagram of example attention mechanisms in accordance with some embodiments.

FIG. 5B illustrates a block diagram 510 of prior attention mechanisms. FIG. 5C illustrates a block diagram 520 of example attention mechanisms in accordance with some embodiments.

FIG. 5B shows prior self-attention layer 512 and prior attention layer 514. Inputs to each of these layers 512, 514 are three weight matrices that are used to project output of a previous layer into a value vector, a key vector, and a value vector.

FIG. 5C shows how the self-attention layer 502 and the attention layer 504 have been adapted or modified. The self-attention layer 502 receives the ingredient embeddings 210 as input and generates contextualized ingredient embeddings. The attention layer 504 receives the output of the self-attention layer 502 (e.g., contextualized ingredient embeddings) and the sensory vector representations 214 as inputs.

Put differently, each ingredient of the base formula queries the desired sensory description so that a corresponding ingredient embedding is modified in terms of the desired sensory description. However, before the ingredients query the desired sensory description, they learn the context they are placed. In other words, each of the ingredients queries all the ingredients in the base formula. The embedding of each ingredient is modified in terms of the context in which the ingredients are placed.

An attention layer outputs the same number of values as the number of input vectors. Since only one ingredient is desired to be output, in some embodiments, there would only be only one vectorized representation for classification.

Figure 5D:
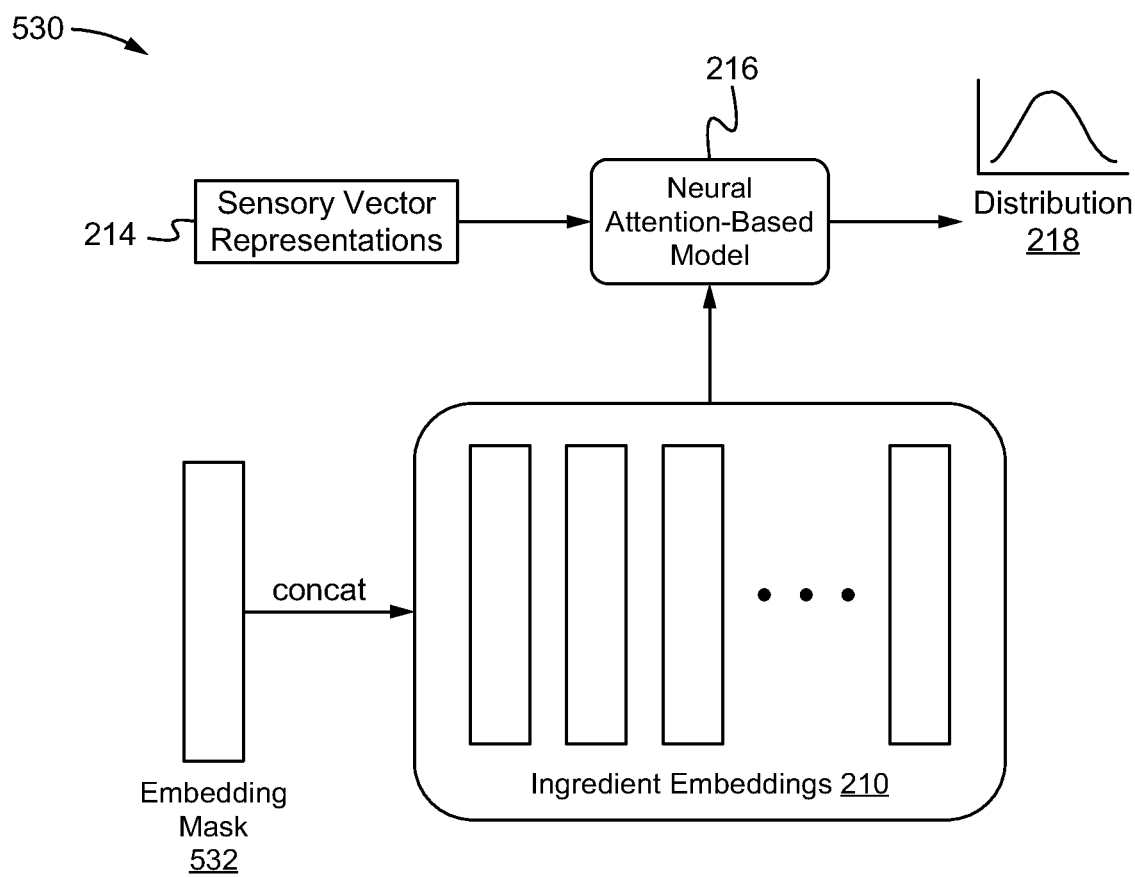
FIG. 5D illustrates a block diagram of an example masked ingredient model in accordance with some embodiments.

FIG. 5D illustrates a block diagram 530 of an example masked ingredient model in accordance with some embodiments. An embedding mask 532 is where classification will occur. The embedding mask 532 is applied (concatenated, added) to the ingredient embeddings 210. The embedding mask 532 also solves the problem of the first ingredient selection or otherwise sets the starting condition because if it is desired to create a formulation from scratch (e.g., no base formula is provided), then there must be an initial embedding to use during classification.

In an embodiment, values of the embedding mask 532 are randomly set. The embedding mask 532 represents the lack of an ingredient in the base formula which will be filled with a new ingredient selected from the distribution of source ingredients determined by the classification layer 506. During training, a loss function, which is a measure of the new ingredient and the masked ingredient, is minimized. An example loss function is the Cross Entropy Loss (CE Loss) function. Other loss functions, such as Kullback-Leibler Divergence Loss, are contemplated.

During inference, an embedding mask is the only one that matters in terms of the second attention mechanism over the sensory description to make a classification since an embedding output from the attention layer 504 is the one that is going to be used as input to the classification layer 506 for selection of one or more candidate ingredients.

It is noted that from a perspective of food science, embedding output from the attention layer 504 contains the features that describe the lack of an ingredient in a formula. These features are modified over the attention mechanisms which first add the information of the relevant ingredients already present in the formula, and then it adds the sensory information to be achieved.

The classification layer 506 of FIG. 5A includes a dense layer that has as many neurons as possible ingredients to be selected and an activation function. The classification layer 506 determines or generates the probability distribution 218 of all possible source ingredients, based on an embedding output from the attention layer 504 (more generally, based on the ingredient embeddings 210 and the sensory vector representations 214). For example, assume there are 830 possible ingredients (e.g., number of source ingredients in the ingredients database 114). The dense layer of the classification layer 506 may have 830 neurons which with the activation function outputs a probability distribution over the 830 ingredients to be selected. An example activation function is a Softmax function, a Sigmoid function, a Tanh function, a ReLU function, etc. As discussed below, K ingredients may be selected or sampled from the probability distribution 218 as candidate ingredients, that could be used during a subsequent formula generation. The K candidate ingredients selected may be those with the highest probability determined from the source ingredients in a fixed search space.

3.1.2 Selector

Figure 6:
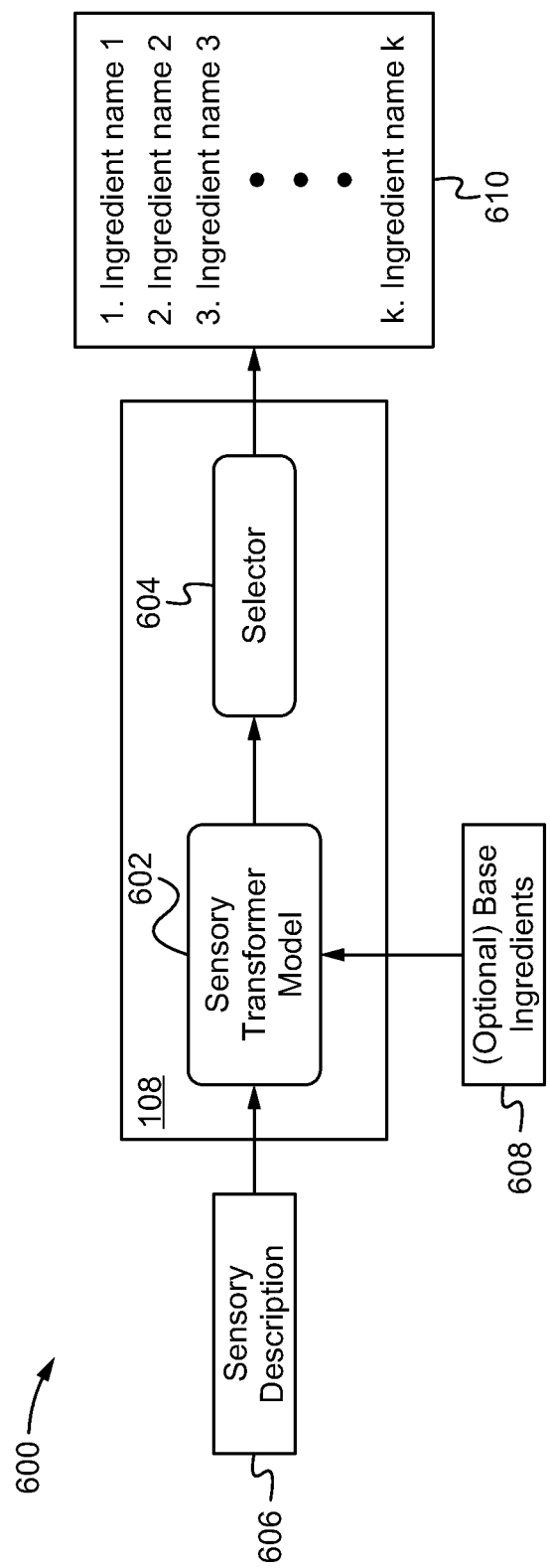
FIG. 6 illustrates a block diagram of an example ingredient generating system in accordance with some embodiments.

FIG. 6 illustrates a block diagram 600 of an example ingredient generating system in accordance with some embodiments. The ingredient generating system includes an ingredients generator, such as the ingredients generator 108. As shown in FIG. 6, the ingredients generator 108 includes a sensory transformer model 602 and a selector 604.

The sensory transformer model 602 may be similarly configured as the sensory model 202 of FIG. 2. For example, the sensory transformer model 602 may include a first neural network language-based model, a second neural network language-based model, and a neural attention-based model. An embodiment of each of these sub-models of the sensory transformer model 602 are discussed above.

The ingredients generator 108 receives a desired sensory description 606 and an optional set of base ingredients 608 as inputs. Using the inputs, the sensory transformer model 602 generates a probability distribution of ingredients (e.g., a discrete probability distribution of all source ingredients in the ingredients database 114).

In an embodiment, the selector 604 selects the top-K ingredients according to the probability calculated by the sensory transformer model 602 (more specifically, a neural attention-based model of the sensory transformer model 602) for each source ingredient in a fixed search space. The ingredients generator 108 returns the top-K ingredients 610 as an output.

The top-K ingredients 610 may be used to modify the set of base ingredients 608. In essence, the ingredients generator 108 guides the set of base ingredients 608 into having or achieving the desired sensory description 606.

3.2 Formulas Generator

Figure 7:
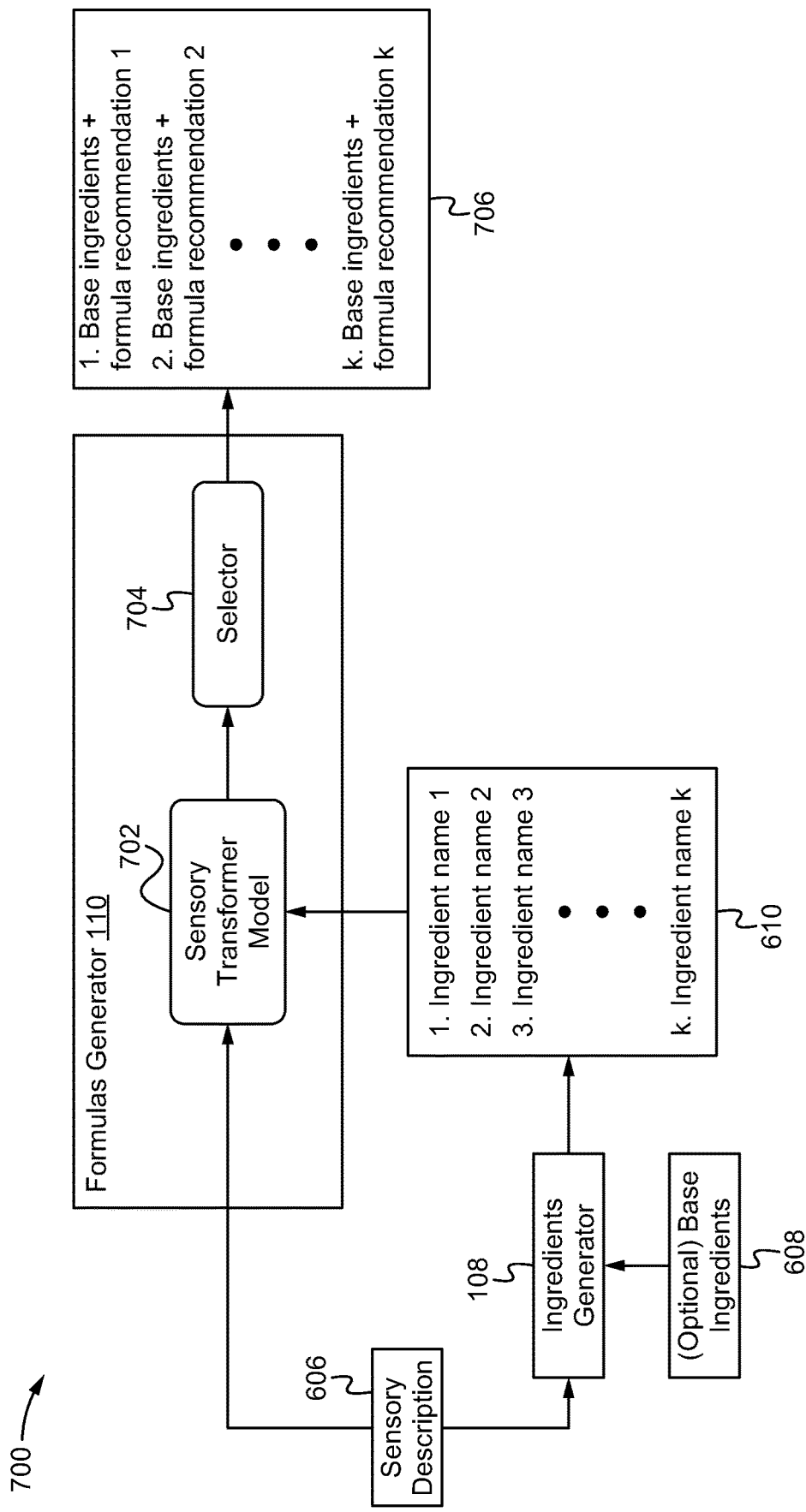
FIG. 7 illustrates a block diagram of an example formula generating system in accordance with some embodiments.

FIG. 7 illustrates a block diagram 700 of an example formula generating system in accordance with some embodiments. The formula generating system includes an ingredients generator, such as the ingredients generator 108, and a formulas generator, such as the formulas generator 110.

As shown in FIG. 7, the formulas generator 110 includes a sensory transformer model 702 and a selector 704.

3.2.1 Sensory Transformer Model

The sensory transformer model 702 of FIG. 7 may be similarly configured as the sensory transformer model 202 of FIG. 2. For example, the sensory transformer model 702 may include a first neural network language-based model, a second neural network language-based model, and a neural attention-based model. An embodiment of each of these sub-models of the sensory transformer model 702 are discussed above.

The formulas generator 110 in FIG. 7 receives the same input data as the ingredients generator 108 (e.g., the desired sensory description 606 and the set of base ingredients 608) receives and, in addition, the top-K ingredients 610 output from the ingredients generator 108 as inputs. The top-K ingredients 610 as the first possible next ingredients are the beginning of M-threads that determine additional ingredients to create complete formulas. In particular, the sensory transformer model 702 generates a probability distribution of all source ingredients, based on the desired sensory profile or description 606 and the top-K ingredients 610, from which the selector 704 selects the next ingredient to add to each candidate formula (formula recommendation).

3.2.2 Selector

In some embodiments, a candidate ingredient of a thread is selected by the selector 704. The selector 704 may include a sampling function, which samples for the next ingredient using the probability calculated by the formulas generator 110 (more specifically, a neural attention-based model of the sensory transformer 702) for each source ingredient in the fixed search space. This "next" ingredient output from the selector 704 is a candidate ingredient that becomes part of a candidate formula (formula recommendation). Each thread iterates the "next" ingredient selection steps n times. At the end of the n iterations, each candidate formula includes n ingredients.

This technique of sampling the next ingredient improves computing performance by minimizing computation of every possible combination. The result of the formulas generator 110 is exactly K candidate formulas in which each candidate formula starts with ingredients extracted from the previous ingredient recommendations stage.

The formulas generator 108 returns K complete formulas 706 as an output. Each of the K complete formulas include the base ingredients, if any, and one of the K candidate formulas.

4.0 EXAMPLE RECOMMENDATIONS

Example 1. Assume that inputs to the server computer 106 of FIG. 1 only include the sensory description "sweet cocoa flavor with creamy texture" (e.g., no base ingredients are input or otherwise provided to the formula generating system). Table 1A shows the top 8 candidate ingredients generated by the ingredients generator 108, while Table 1B shows example the top 8 candidate formulas generated by the formulas generator 110. In an embodiments, the candidate ingredients and candidate formulas are displayed in a graphical user interface of the client device 104 of FIG. 1.

TABLE 1A

| Ingredient | Probability [%] |
| --- | --- |
| peanut butter, smooth | 38.5 |
| cocoa powder, unsweetened | 18.8 |
| walnut | 13.9 |
| almond oil | 7.9 |
| sunflower oil | 4.9 |
| popcorn powder (with sugar) | 1.9 |
| whole not milk | 1.9 |
| bitter chocolate chips | 1.4 |

TABLE 1B

| Formula Recommendations | Probability [%] |
| --- | --- |
| walnut, bitter chocolate, 71% cacao, whole wheat flour | 1.18 |
| cocoa powder, unsweetened, almond oil, sugar, powder | 1.03 |
| peanut butter, smooth, bitter chocolate chips, baking powder | 0.82 |
| popcorn powder (with sugar), pineapple juice, peanut butter, smooth | 0.23 |
| tomato juice, cocoa powder, unsweetened, almond oil | 0.11 |
| sunflower oil, cocoa powder, unsweetened, ground hazelnut | 0.09 |
| almond oil, quince, jam, cocoa powder, unsweetened | 0.09 |
| whole not milk, bitter chocolate chips, sugar, powder | 0.04 |

Example 2. Assume that inputs to server computer 106 of FIG. 1 include the sensory description "cooked vegetable, salty flavor with potato and vegetable smell and with fluid, soft and tender texture" and with base ingredients including potato, salt, yellow corn, and water. Table 2A shows the top 8 candidate ingredients generated by the ingredients generator 108, while Table 2B shows example the top 8 candidate formulas generated by the formulas generator 110. In an embodiments, the candidate ingredients and candidate formulas are displayed in a graphical user interface of the client computer 104 of FIG. 1.

TABLE 2A

| Ingredient | Probability [%] |
| --- | --- |
| spinach | 84.9 |
| semolina | 1.8 |
| gellan gum | 1.0 |
| pickled cucumber | 0.8 |
| paris mushroom | 0.8 |
| peanut butter, smooth | 0.5 |
| pea protein powder | 0.4 |
| pumpkin | 0.4 |

TABLE 2B

| Formula Recommendations | Probability [%] |
| --- | --- |
| gellan gum, methylcellulose (solucel b5 - blumos), pumpkin | 0.34 |
| semolina, spinach, pumpkin | 0.08 |
| pea protein (powder), spinach, gellan gum | 0.07 |
| pumpkin, spinach, gellan gum | 0.06 |
| turnip, black beans, canned, pea protein (powder) | 0.04 |
| spinach, pea protein (powder), capers, canned | 0.03 |
| paris mushroom, spinach, heart of palm | 0.02 |
| pickled cucumber, spinach, mustard oil | 0.02 |

5.1 Procedural Overview

Figure 8:
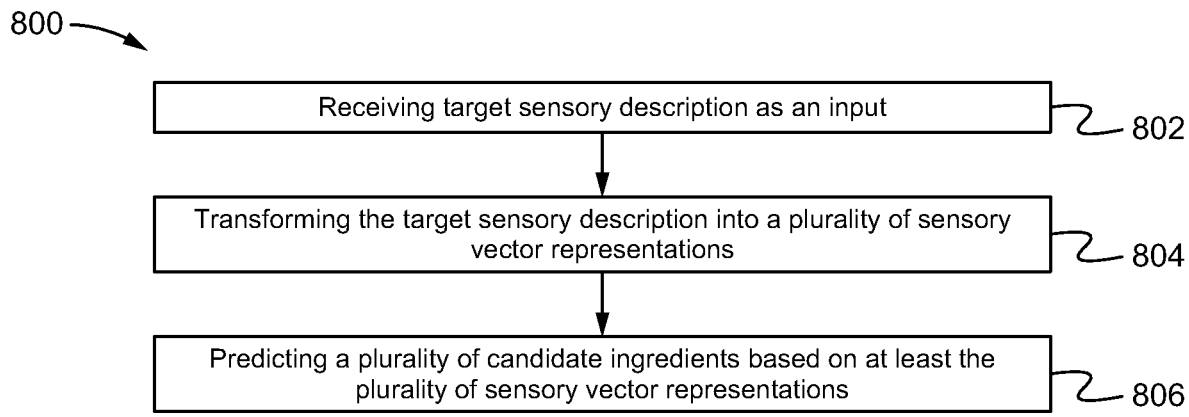
FIG. 8 illustrates an example method to generate candidate ingredients in accordance with some embodiments.

FIG. 8 illustrates an example method 800 to generate candidate ingredients for a target sensory description, in accordance with some embodiments. FIG. 8 may be used as a basis to code the method 800 as one or more computer programs or other software elements that a server computer can execute or host.

At Step 802, an ingredients machine learning model receives a target sensory description as an input. In an embodiment, the target sensory description is received in raw text format. For example, the ingredients machine learning model is the ingredients generator 108, which receives the target sensory description. An example sensory description is "creamy texture and sweet flavor."

In an embodiment, the ingredients machine learning model may also receive base ingredients as inputs. In an embodiment, the base ingredients are received in raw text format. The base ingredients are ingredients in a base formula that may be enhanced (modified) such that a resulting food product has (achieves) the target sensory description.

The target sensory description and any the base ingredients may be input from a client computer, such as client device 104.

At Step 804, the ingredients machine learning model transforms the target sensory description into a plurality of sensory vector representations. For example, the second neural network language-based model of the ingredients generator 108 encodes the target sensory description into the plurality of sensory vector representations.

In an embodiment, the ingredients machine learning model also transforms any base ingredients received at Step 802 into a plurality of ingredient embeddings. For example, the first neural network language-based model of the ingredients generator 108 encodes the base ingredients in a space that contains sensory data, into the plurality of ingredient embeddings.

As described herein, the first neural network language-based model and the second neural network language-based model are configured as the encoder of the ingredients generator 108.

At Step 806, the ingredients machine learning model predicts a plurality of candidate ingredients based on the plurality of sensory vector representations and, if any, the plurality of ingredient embeddings from Step 804. For example, the neural attention-based model of the ingredients generator 108 receives the plurality of sensory vector representations and, if any, the plurality of ingredient embeddings, generates a probability distribution of source ingredients (e.g., source ingredients from the ingredients database 114), and outputs the top-K ingredients from the distribution as candidate ingredients. These candidate ingredients may be used to generate sets of ingredients (complete formulas) that when ingredients in each set is combined become a food product that has or achieves the target sensory description.

As described herein, the neural attention-based model is configured as the decoder of the ingredients generator 108.

In an embodiment, the candidate ingredients may be displayed in a graphical user interface of the client device 104.

Figure 9:
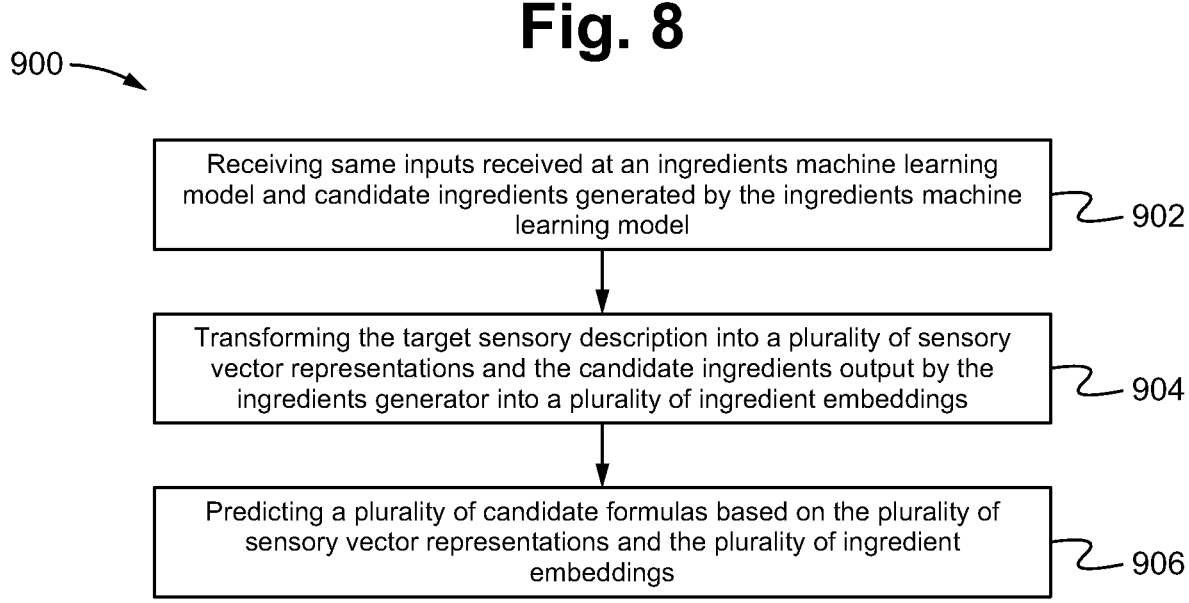
FIG. 9 illustrates an example method to generate candidate formulas in accordance with some embodiments.

FIG. 9 illustrates an example method 900 to generate candidate formulas for a target sensory description, in accordance with some embodiments. FIG. 9 may be used as a basis to code the method 900 as one or more computer programs or other software elements that a server computer can execute or host.

At Step 902, a formulas machine learning model receives the same inputs received at an ingredients machine learning model and candidate ingredients generated by the ingredients machine learning model as inputs. For example, the formulas machine learning model is the formulas generator 110, which receives a target sensory description, any base ingredients, and candidate ingredients generated by the ingredients generator 108. An example method of generating candidate ingredients is described at least in FIG. 8.

In an embodiment, any base ingredients become part of a complete formula such that when ingredients in the complete formula are combined become a food product with the target sensory description.

At Step 904, the formulas machine learning model transforms the target sensory description into a plurality of sensory vector representations. For example, the second neural network language-based model of the formulas generator 110 encodes the target sensory description into the plurality of sensory vector representations.

Also at Step 904, the formulas machine learning model also transforms the candidate ingredients output by the ingredients generator 108 into a plurality of ingredient embeddings. For example, the first neural network language-based model of the formulas generator 110 encodes these candidate ingredients in a space that contains sensory data, into the plurality of ingredient embeddings.

As described herein, the first neural network language-based model and the second neural network language-based model are configured as the encoder of the formulas generator 110.

At Step 906, the formula machine learning model predicts a plurality of candidate formulas based on the plurality of sensory vector representations and the plurality of ingredient embeddings from Step 904. For example, the neural attention-based model of the formulas generator 110 receives the plurality of sensory vector representations and the plurality of ingredient embeddings, generates a probability distribution of source ingredients (e.g., source ingredients from the ingredients database 114), and outputs n ingredients sampled from the distribution as candidate ingredients. These candidate ingredients are added to a candidate formula (formula recommendation). In an embodiment, the formula machine learning model iterates n times to generate the n ingredients.

As described herein, the neural attention-based model is configured as the decoder of the formulas generator 110.

In an embodiment, the candidate formula may be displayed in a graphical user interface of the client device 104.

The base ingredients (collectively, base formula) together with the candidate formula are referred to herein as a complete formula. Ingredients in the complete formula are combined to become a food product that has or achieves the target sensory description.

In an embodiment, the formula machine learning model uses K-threads to predict K candidate formulas. In an embodiment, the candidate formulas may be displayed in a graphical user interface of the client device 104.

Techniques described herein address challenges of developing plant-based products given a base formula, by guiding the base formula towards a desired (target) sensory profile. Techniques provide a solution where a sensory text description may be received and candidate ingredients are predicted, based on the description and an optional actual state of formula (base formula) to be improved. As described herein, a sensory transformer model includes a previously trained language model as an encoder and two learnt attention layers as a decoder. The encoder also includes a learned dense layer that projects ingredient vector representations of the language model into an encoded space that contains sensory data, transforming the ingredient vector representations into ingredient embeddings that contain sensory features. The encoder and the decoder form the sensory transformer model, which recommends (generates, predicts, determines) ingredients one by one, which thereby enables recommendation of the most probable ingredients to be selected for candidate formulas. When ingredients in each set of ingredients, including a candidate formula and the base formula, are combined into a food product, the food product has the desired sensory profile.

6.0 HARDWARE OVERVIEW

According to one embodiment, the techniques described herein are implemented by at least one computing device. The techniques may be implemented in whole or in part using a combination of at least one server computer and/or other computing devices that are coupled using a network, such as a packet data network. The computing devices may be hard-wired to perform the techniques or may include digital electronic devices such as at least one application-specific integrated circuit (ASIC) or field programmable gate array (FPGA) that is persistently programmed to perform the techniques or may include at least one general purpose hardware processor programmed to perform the techniques pursuant to program instructions in firmware, memory, other storage, or a combination. Such computing devices may also combine custom hard-wired logic, ASICs, or FPGAs with custom programming to accomplish the described techniques. The computing devices may be server computers, workstations, personal computers, portable computer systems, handheld devices, mobile computing devices, wearable devices, body mounted or implantable devices, smartphones, smart appliances, internetworking devices, autonomous or semi-autonomous devices such as robots or unmanned ground or aerial vehicles, any other electronic device that incorporates hard-wired and/or program logic to implement the described techniques, one or more virtual computing machines or instances in a data center, and/or a network of server computers and/or personal computers.

Figure 10:
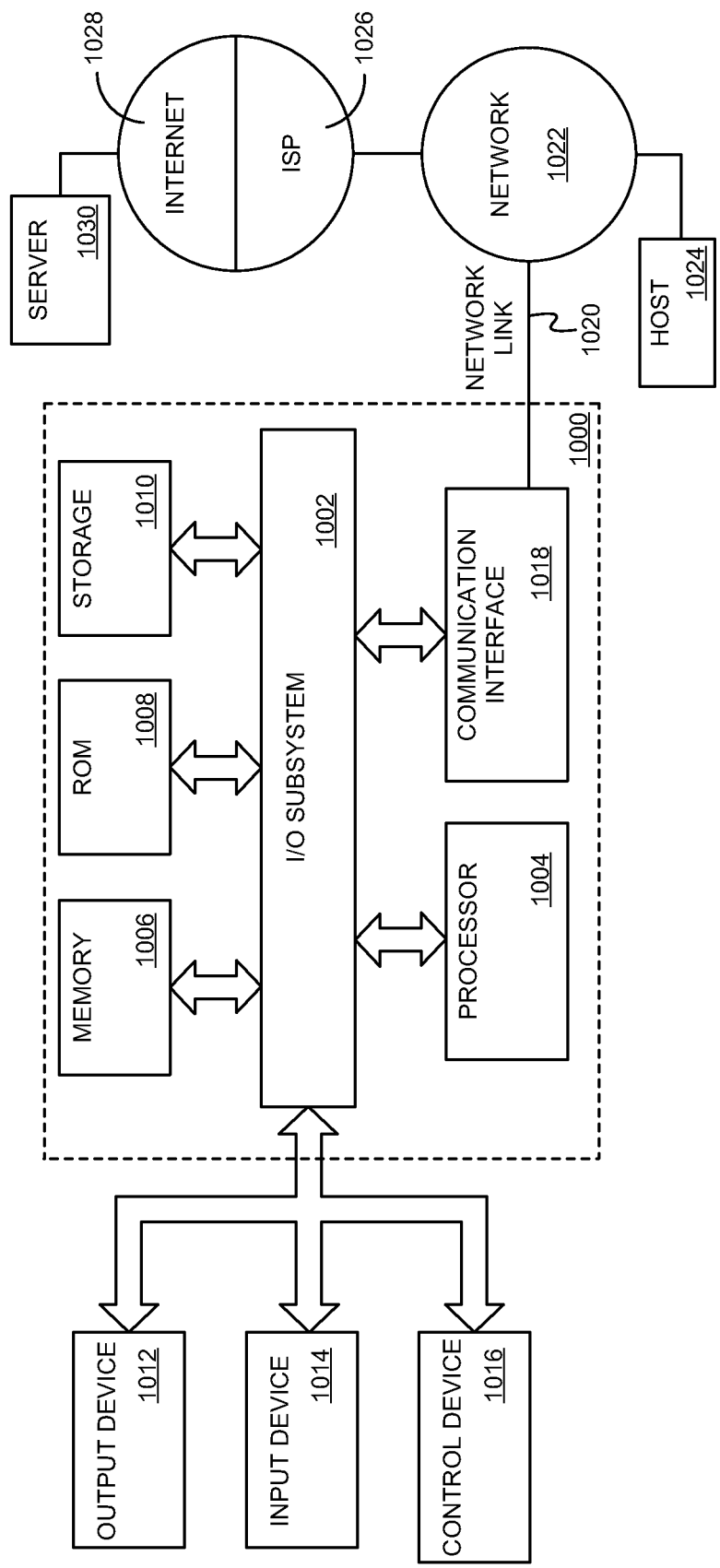
FIG. 10 illustrates a block diagram of a computing device in which the example embodiment(s) of the present invention may be embodiment.

FIG. 10 is a block diagram that illustrates an example computer system with which an embodiment may be implemented. In the example of FIG. 10, a computer system 1000 and instructions for implementing the disclosed technologies in hardware, software, or a combination of hardware and software, are represented schematically, for example as boxes and circles, at the same level of detail that is commonly used by persons of ordinary skill in the art to which this disclosure pertains for communicating about computer architecture and computer systems implementations.

Computer system 1000 includes an input/output (I/O) subsystem 1002 which may include a bus and/or other communication mechanism(s) for communicating information and/or instructions between the components of the computer system 1000 over electronic signal paths. The I/O subsystem 1002 may include an I/O controller, a memory controller and at least one I/O port. The electronic signal paths are represented schematically in the drawings, for example as lines, unidirectional arrows, or bidirectional arrows.

At least one hardware processor 1004 is coupled to I/O subsystem 1002 for processing information and instructions. Hardware processor 1004 may include, for example, a general-purpose microprocessor or microcontroller and/or a special-purpose microprocessor such as an embedded system or a graphics processing unit (GPU) or a digital signal processor or ARM processor. Processor 1004 may comprise an integrated arithmetic logic unit (ALU) or may be coupled to a separate ALU.

Computer system 1000 includes one or more units of memory 1006, such as a main memory, which is coupled to I/O subsystem 1002 for electronically digitally storing data and instructions to be executed by processor 1004. Memory 1006 may include volatile memory such as various forms of random-access memory (RAM) or other dynamic storage device. Memory 1006 also may be used for storing temporary variables or other intermediate information during execution of instructions to be executed by processor 1004. Such instructions, when stored in non-transitory computer-readable storage media accessible to processor 1004, can render computer system 1000 into a special-purpose machine that is customized to perform the operations specified in the instructions.

Computer system 1000 further includes non-volatile memory such as read only memory (ROM) 1008 or other static storage device coupled to I/O subsystem 1002 for storing information and instructions for processor 1004. The ROM 1008 may include various forms of programmable ROM (PROM) such as erasable PROM (EPROM) or electrically erasable PROM (EEPROM). A unit of persistent storage 1010 may include various forms of non-volatile RAM (NVRAM), such as FLASH memory, or solid-state storage, magnetic disk, or optical disk such as CD-ROM or DVD-ROM and may be coupled to I/O subsystem 1002 for storing information and instructions. Storage 1010 is an example of a non-transitory computer-readable medium that may be used to store instructions and data which when executed by the processor 1004 cause performing computer-implemented methods to execute the techniques herein.

The instructions in memory 1006, ROM 1008 or storage 1010 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to parse or render files coded using HTML, XML, JPEG, MPEG or PNG; user interface instructions to render or interpret commands for a graphical user interface (GUI), command-line interface or text user interface; application software such as an office suite, internet access applications, design and manufacturing applications, graphics applications, audio applications, software engineering applications, educational applications, games or miscellaneous applications. The instructions may implement a web server, web application server or web client. The instructions may be organized as a presentation layer, application layer and data storage layer such as a relational database system using structured query language (SQL) or no SQL, an object store, a graph database, a flat file system or other data storage.

Computer system 1000 may be coupled via I/O subsystem 1002 to at least one output device 1012. In one embodiment, output device 1012 is a digital computer display. Examples of a display that may be used in various embodiments include a touch screen display or a light-emitting diode (LED) display or a liquid crystal display (LCD) or an e-paper display. Computer system 1000 may include other type(s) of output devices 1012, alternatively or in addition to a display device. Examples of other output devices 1012 include printers, ticket printers, plotters, projectors, sound cards or video cards, speakers, buzzers or piezoelectric devices or other audible devices, lamps or LED or LCD indicators, haptic devices, actuators, or servos.

At least one input device 1014 is coupled to I/O subsystem 1002 for communicating signals, data, command selections or gestures to processor 1004. Examples of input devices 1014 include touch screens, microphones, still and video digital cameras, alphanumeric and other keys, keypads, keyboards, graphics tablets, image scanners, joysticks, clocks, switches, buttons, dials, slides, and/or various types of sensors such as force sensors, motion sensors, heat sensors, accelerometers, gyroscopes, and inertial measurement unit (IMU) sensors and/or various types of transceivers such as wireless, such as cellular or Wi-Fi, radio frequency (RF) or infrared (IR) transceivers and Global Positioning System (GPS) transceivers.

Another type of input device is a control device 1016, which may perform cursor control or other automated control functions such as navigation in a graphical interface on a display screen, alternatively or in addition to input functions. Control device 1016 may be a touchpad, a mouse, a trackball, or cursor direction keys for communicating direction information and command selections to processor 1004 and for controlling cursor movement on display. The input device may have at least two degrees of freedom in two axes, a first axis (e.g., x) and a second axis (e.g., y), that allows the device to specify positions in a plane. Another type of input device is a wired, wireless, or optical control device such as a joystick, wand, console, steering wheel, pedal, gearshift mechanism or other type of control device. An input device 1014 may include a combination of multiple different input devices, such as a video camera and a depth sensor.

In another embodiment, computer system 1000 may comprise an internet of things (IoT) device in which one or more of the output device 1012, input device 1014, and control device 1016 are omitted. Or, in such an embodiment, the input device 1014 may comprise one or more cameras, motion detectors, thermometers, microphones, seismic detectors, other sensors or detectors, measurement devices or encoders and the output device 1012 may comprise a special-purpose display such as a single-line LED or LCD display, one or more indicators, a display panel, a meter, a valve, a solenoid, an actuator or a servo.

When computer system 1000 is a mobile computing device, input device 1014 may comprise a global positioning system (GPS) receiver coupled to a GPS module that is capable of triangulating to a plurality of GPS satellites, determining and generating geo-location or position data such as latitude-longitude values for a geophysical location of the computer system 1000. Output device 1012 may include hardware, software, firmware and interfaces for generating position reporting packets, notifications, pulse or heartbeat signals, or other recurring data transmissions that specify a position of the computer system 1000, alone or in combination with other application-specific data, directed toward host 1024 or server 1030.

Computer system 1000 may implement the techniques described herein using customized hard-wired logic, at least one ASIC or FPGA, firmware and/or program instructions or logic which when loaded and used or executed in combination with the computer system causes or programs the computer system to operate as a special-purpose machine. According to one embodiment, the techniques herein are performed by computer system 1000 in response to processor 1004 executing at least one sequence of at least one instruction contained in main memory 1006. Such instructions may be read into main memory 1006 from another storage medium, such as storage 1010. Execution of the sequences of instructions contained in main memory 1006 causes processor 1004 to perform the process steps described herein. In alternative embodiments, hard-wired circuitry may be used in place of or in combination with software instructions.

The term "storage media" as used herein refers to any non-transitory media that store data and/or instructions that cause a machine to operation in a specific fashion. Such storage media may comprise non-volatile media and/or volatile media. Non-volatile media includes, for example, optical or magnetic disks, such as storage 1010. Volatile media includes dynamic memory, such as memory 1006. Common forms of storage media include, for example, a hard disk, solid state drive, flash drive, magnetic data storage medium, any optical or physical data storage medium, memory chip, or the like.

Storage media is distinct from but may be used in conjunction with transmission media. Transmission media participates in transferring information between storage media. For example, transmission media includes coaxial cables, copper wire and fiber optics, including the wires that comprise a bus of I/O subsystem 1002. Transmission media can also take the form of acoustic or light waves, such as those generated during radio-wave and infra-red data communications.

Various forms of media may be involved in carrying at least one sequence of at least one instruction to processor 1004 for execution. For example, the instructions may initially be carried on a magnetic disk or solid-state drive of a remote computer. The remote computer can load the instructions into its dynamic memory and send the instructions over a communication link such as a fiber optic or coaxial cable or telephone line using a modem. A modem or router local to computer system 1000 can receive the data on the communication link and convert the data to a format that can be read by computer system 1000. For instance, a receiver such as a radio frequency antenna or an infrared detector can receive the data carried in a wireless or optical signal and appropriate circuitry can provide the data to I/O subsystem 1002 such as place the data on a bus. I/O subsystem 1002 carries the data to memory 1006, from which processor 1004 retrieves and executes the instructions. The instructions received by memory 1006 may optionally be stored on storage 1010 either before or after execution by processor 1004.

Computer system 1000 also includes a communication interface 1018 coupled to bus 1002. Communication interface 1018 provides a two-way data communication coupling to network link(s) 1020 that are directly or indirectly connected to at least one communication networks, such as a network 1022 or a public or private cloud on the Internet. For example, communication interface 1018 may be an Ethernet networking interface, integrated-services digital network (ISDN) card, cable modem, satellite modem, or a modem to provide a data communication connection to a corresponding type of communications line, for example an Ethernet cable or a metal cable of any kind or a fiber-optic line or a telephone line. Network 1022 broadly represents a local area network (LAN), wide-area network (WAN), campus network, internetwork, or any combination thereof. Communication interface 1018 may comprise a LAN card to provide a data communication connection to a compatible LAN, or a cellular radiotelephone interface that is wired to send or receive cellular data according to cellular radiotelephone wireless networking standards, or a satellite radio interface that is wired to send or receive digital data according to satellite wireless networking standards. In any such implementation, communication interface 1018 sends and receives electrical, electromagnetic, or optical signals over signal paths that carry digital data streams representing various types of information.

Network link 1020 typically provides electrical, electromagnetic, or optical data communication directly or through at least one network to other data devices, using, for example, satellite, cellular, Wi-Fi, or BLUETOOTH technology. For example, network link 1020 may provide a connection through a network 1022 to a host computer 1024.

Furthermore, network link 1020 may provide a connection through network 1022 or to other computing devices via internetworking devices and/or computers that are operated by an Internet Service Provider (ISP) 1026. ISP 1026 provides data communication services through a world-wide packet data communication network represented as internet 1028. A server computer 1030 may be coupled to internet 1028. Server 1030 broadly represents any computer, data center, virtual machine, or virtual computing instance with or without a hypervisor, or computer executing a containerized program system such as DOCKER or KUBERNETES. Server 1030 may represent an electronic digital service that is implemented using more than one computer or instance and that is accessed and used by transmitting web services requests, uniform resource locator (URL) strings with parameters in HTTP payloads, API calls, app services calls, or other service calls. Computer system 1000 and server 1030 may form elements of a distributed computing system that includes other computers, a processing cluster, server farm or other organization of computers that cooperate to perform tasks or execute applications or services.

Server 1030 may comprise one or more sets of instructions that are organized as modules, methods, objects, functions, routines, or calls. The instructions may be organized as one or more computer programs, operating system services, or application programs including mobile apps. The instructions may comprise an operating system and/or system software; one or more libraries to support multimedia, programming or other functions; data protocol instructions or stacks to implement TCP/IP, HTTP or other communication protocols; file format processing instructions to parse or render files coded using HTML, XML, JPEG, MPEG or PNG; user interface instructions to render or interpret commands for a graphical user interface (GUI), command-line interface or text user interface; application software such as an office suite, internet access applications, design and manufacturing applications, graphics applications, audio applications, software engineering applications, educational applications, games or miscellaneous applications. Server 1030 may comprise a web application server that hosts a presentation layer, application layer and data storage layer such as a relational database system using structured query language (SQL) or no SQL, an object store, a graph database, a flat file system or other data storage.

Computer system 1000 can send messages and receive data and instructions, including program code, through the network(s), network link 1020 and communication interface 1018. In the Internet example, a server 1030 might transmit a requested code for an application program through Internet 1028, ISP 1026, local network 1022 and communication interface 1018. The received code may be executed by processor 1004 as it is received, and/or stored in storage 1010, or other non-volatile storage for later execution.

The execution of instructions as described in this section may implement a process in the form of an instance of a computer program that is being executed and consisting of program code and its current activity. Depending on the operating system (OS), a process may be made up of multiple threads of execution that execute instructions concurrently. In this context, a computer program is a passive collection of instructions, while a process may be the actual execution of those instructions. Several processes may be associated with the same program; for example, opening up several instances of the same program often means more than one process is being executed. Multitasking may be implemented to allow multiple processes to share processor 1004. While each processor 1004 or core of the processor executes a single task at a time, computer system 1000 may be programmed to implement multitasking to allow each processor to switch between tasks that are being executed without having to wait for each task to finish. In an embodiment, switches may be performed when tasks perform input/output operations, when a task indicates that it can be switched, or on hardware interrupts. Time-sharing may be implemented to allow fast response for interactive user applications by rapidly performing context switches to provide the appearance of concurrent execution of multiple processes simultaneously. In an embodiment, for security and reliability, an operating system may prevent direct communication between independent processes, providing strictly mediated and controlled inter-process communication functionality.

7.0 SOFTWARE OVERVIEW

Figure 11:
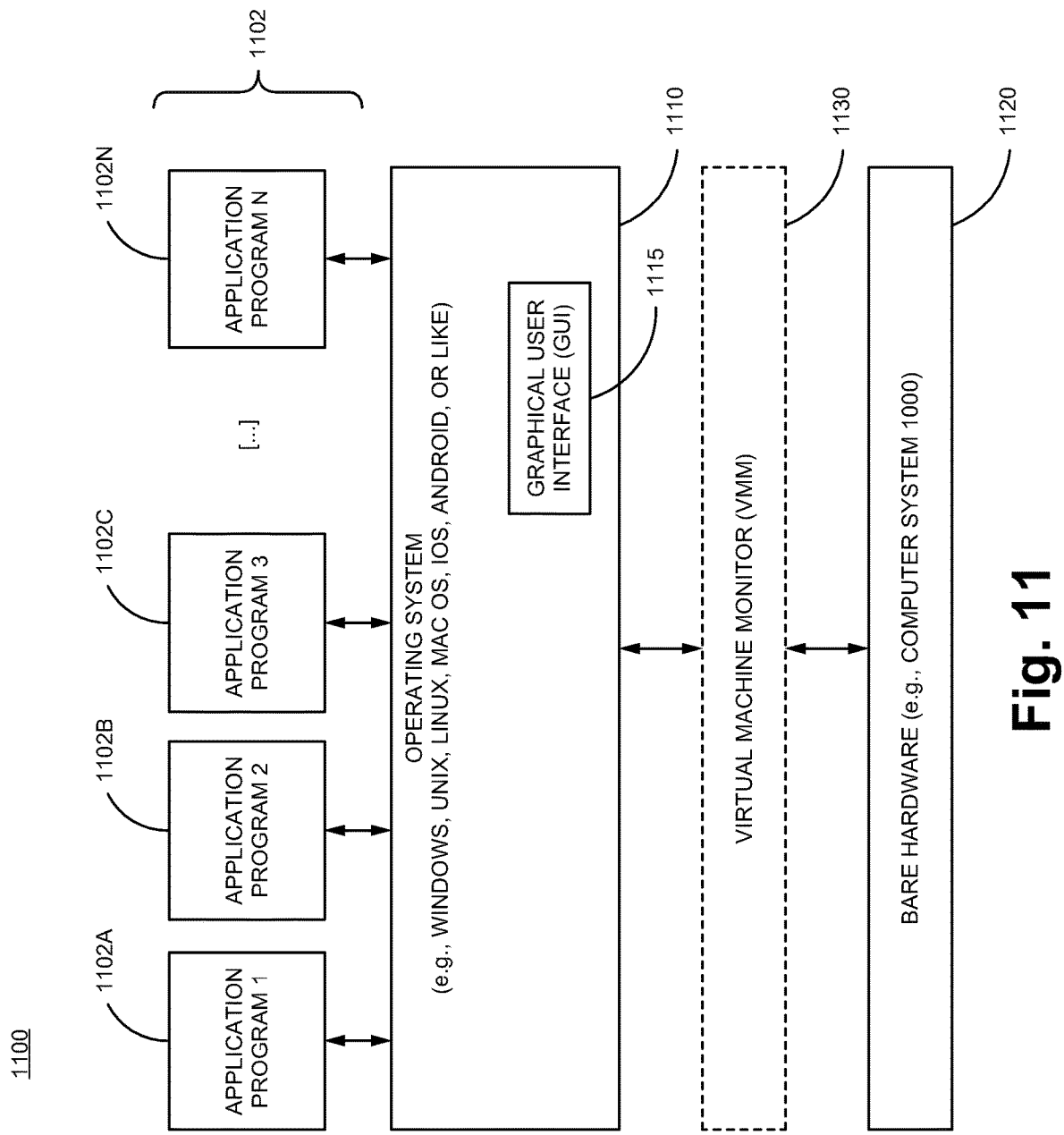
FIG. 11 illustrates a block diagram of a basic software system for controlling the operation of a computing device.

FIG. 11 is a block diagram of a basic software system 1100 that may be employed for controlling the operation of computing device 1000. Software system 1100 and its components, including their connections, relationships, and functions, is meant to be exemplary only, and not meant to limit implementations of the example embodiment(s). Other software systems suitable for implementing the example embodiment(s) may have different components, including components with different connections, relationships, and functions.

Software system 1100 is provided for directing the operation of computing device 1000. Software system 1100, which may be stored in system memory (RAM) 1006 and on fixed storage (e.g., hard disk or flash memory) 1010, includes a kernel or operating system (OS) 1110.

The OS 1110 manages low-level aspects of computer operation, including managing execution of processes, memory allocation, file input and output (I/O), and device I/O. One or more application programs, represented as 1102A, 1102B, 1102C . . . 1102N, may be "loaded" (e.g., transferred from fixed storage 1010 into memory 1006) for execution by the system 1100. The applications or other software intended for use on device 1100 may also be stored as a set of downloadable computer-executable instructions, for example, for downloading and installation from an Internet location (e.g., a Web server, an app store, or other online service).

Software system 1100 includes a graphical user interface (GUI) 1115, for receiving user commands and data in a graphical (e.g., "point-and-click" or "touch gesture") fashion. These inputs, in turn, may be acted upon by the system 1100 in accordance with instructions from operating system 1110 and/or application(s) 1102. The GUI 1115 also serves to display the results of operation from the OS 1110 and application(s) 1102, whereupon the user may supply additional inputs or terminate the session (e.g., log off).

OS 1110 can execute directly on the bare hardware 1120 (e.g., processor(s) 1004) of device 1000. Alternatively, a hypervisor or virtual machine monitor (VMM) 1130 may be interposed between the bare hardware 1120 and the OS 1110. In this configuration, VMM 1130 acts as a software "cushion" or virtualization layer between the OS 1110 and the bare hardware 1120 of the device 1000.

VMM 1130 instantiates and runs one or more virtual machine instances ("guest machines"). Each guest machine comprises a "guest" operating system, such as OS 1110, and one or more applications, such as application(s) 1102, designed to execute on the guest operating system. The VMM 1130 presents the guest operating systems with a virtual operating platform and manages the execution of the guest operating systems.

In some instances, the VMM 1130 may allow a guest operating system to run as if it is running on the bare hardware 1120 of device 1000 directly. In these instances, the same version of the guest operating system configured to execute on the bare hardware 1120 directly may also execute on VMM 1130 without modification or reconfiguration. In other words, VMM 1130 may provide full hardware and CPU virtualization to a guest operating system in some instances.

In other instances, a guest operating system may be specially designed or configured to execute on VMM 1130 for efficiency. In these instances, the guest operating system is "aware" that it executes on a virtual machine monitor. In other words, VMM 1130 may provide para-virtualization to a guest operating system in some instances.

The above-described basic computer hardware and software is presented for purpose of illustrating the basic underlying computer components that may be employed for implementing the example embodiment(s). The example embodiment(s), however, are not necessarily limited to any particular computing environment or computing device configuration. Instead, the example embodiment(s) may be implemented in any type of system architecture or processing environment that one skilled in the art, in light of this disclosure, would understand as capable of supporting the features and functions of the example embodiment(s) presented herein.

8.0 OTHER ASPECTS OF DISCLOSURE

Although some of the figures described in the foregoing specification include flow diagrams with steps that are shown in an order, the steps may be performed in any order, and are not limited to the order shown in those flowcharts. Additionally, some steps may be optional, may be performed multiple times, and/or may be performed by different components. All steps, operations and functions of a flow diagram that are described herein are intended to indicate operations that are performed using programming in a special-purpose computer or general-purpose computer, in various embodiments. In other words, each flow diagram in this disclosure, in combination with the related text herein, is a guide, plan or specification of all or part of an algorithm for programming a computer to execute the functions that are described. The level of skill in the field associated with this disclosure is known to be high, and therefore the flow diagrams and related text in this disclosure have been prepared to convey information at a level of sufficiency and detail that is normally expected in the field when skilled persons communicate among themselves with respect to programs, algorithms and their implementation.

In the foregoing specification, the example embodiment(s) of the present invention have been described with reference to numerous specific details. However, the details may vary from implementation to implementation according to the requirements of the particular implement at hand. The example embodiment(s) are, accordingly, to be regarded in an illustrative rather than a restrictive sense.

What is claimed is:

1. A computer-implemented method comprising
   applying an artificial intelligence model to first digital data representing base ingredients and second digital data representing a target sensory description, wherein the artificial intelligence model comprises:
   a sensory transformer model generating a probability distribution of source ingredients based on an embedding associated with the first digital data representing the base ingredients and the second digital data representing the target sensory description, wherein the sensory transformer model comprises
   an encoder that includes a first neural network language-based model outputting the first digital data representing the base ingredients and a second neural network language-based model outputting the second digital data representing the target sensory description, and
   a decoder that includes a neural attention-based model using the first digital data and the second digital data to determine the embedding for generating the probability distribution of source ingredients; and
   a selector selecting at least one candidate ingredient from the probability distribution of source ingredients;
   in response to applying the artificial intelligence model, identifying the at least one candidate ingredient, wherein a complete set of ingredients generated based on the at least one candidate ingredient when combined becomes a food product having the target sensory description.

2. The method of claim 1, wherein the first digital data is obtained by applying the first neural network language-based model to names of the base ingredients, and the second digital data is obtained by applying the second neural network language-based model to the target sensory description.

3. The method of claim 1, wherein the first neural network language-based model comprises a language model and a dense layer, wherein [CLS] token representations generated by the language model are used to train the dense layer.

4. The method of claim 1, wherein the neural attention-based model comprises a plurality of attention layers and a classification layer.

5. The method of claim 4, wherein the embedding is generated by applying the plurality of attention layers to the first digital data representing the base ingredients and the second digital data representing the target sensory description.

6. The method of claim 4, wherein the probability distribution of source ingredients is generated by the classification layer for the embedding.

7. One or more non-transitory computer-readable storage media storing one or more instructions programmed, when executed by one or more computing devices, cause:
applying an artificial intelligence model to first digital data representing base ingredients and second digital data representing a target sensory description, wherein the artificial intelligence model comprises:
a sensory transformer model generating a probability distribution of source ingredients based on an embedding associated with the first digital data representing the base ingredients and the second digital data representing the target sensory description, wherein the sensory transformer model comprises
an encoder that includes a first neural network language-based model outputting the first digital data representing the base ingredients and a second neural network language-based model outputting the second digital data representing the target sensory description, and
a decoder that includes a neural attention-based model using the first digital data and the second digital data to determine the embedding for generating the probability distribution of source ingredients; and
a selector selecting at least one candidate ingredient from the probability distribution of source ingredients;
in response to applying the artificial intelligence model, identifying the at least one candidate ingredient, wherein a complete set of ingredients generated based on the at least one candidate ingredient when combined becomes a food product having the target sensory description.

8. The one or more non-transitory computer-readable storage media of claim 7, wherein the first digital data is obtained by applying the first neural network language-based model to names of the base ingredients, and the second digital data is obtained by applying the second neural network language-based model to the sensory description.

9. The one or more non-transitory computer-readable storage media of claim 7, wherein the first neural network language-based model comprises a language model and a dense layer, wherein token representations generated by the language model are used to train the dense layer.

10. The one or more non-transitory computer-readable storage media of claim 7, wherein the neural attention-based model comprises a plurality of attention layers and a classification layer.

11. The one or more non-transitory computer-readable storage media of claim 10, wherein the embedding is generated by applying the plurality of attention layers to the first digital data representing the base ingredients and the second digital data representing the target sensory description.

12. The one or more non-transitory computer-readable storage media of claim 10, wherein the probability distribution of source ingredients is generated by the classification layer for the embedding.

13. A computing system comprising:
one or more computer systems comprising one or more hardware processors and storage media; and
instructions stored in the storage media and which, when executed by the computing system, cause the computing system to perform:
applying an artificial intelligence model to first digital data representing base ingredients and second digital data representing a target sensory description, wherein the artificial intelligence model comprises:
a sensory transformer model generating a probability distribution of source ingredients based on an embedding associated with the first digital data representing the base ingredients and the second digital data representing the target sensory description, wherein the sensory transformer model comprises
an encoder that includes a first neural network language-based model outputting the first digital data representing the base ingredients and a second neural network language-based model outputting the second digital data representing the target sensory description, and
a decoder that includes a neural attention-based model using the first digital data and the second digital data to determine the embedding for generating the probability distribution of source ingredients; and
a selector selecting at least one candidate ingredient from the probability distribution of source ingredients;
in response to applying the artificial intelligence model, identifying the at least one candidate ingredient, wherein a complete set of ingredients generated based on the at least one candidate ingredient when combined becomes a food product having the target sensory description.

14. The computing system of claim 13, wherein the first digital data is obtained by applying the first neural network language-based model to names of the base ingredients, and the second digital data is obtained by applying the second neural network language-based model to the target sensory description.

15. The computing system of claim 13, wherein the first neural network language-based model comprises a language model and a dense layer, wherein token representations generated by the language model are used to train the dense layer.

16. The computing system of claim 13, wherein the neural attention-based model comprises a plurality of attention layers and a classification layer.

17. The computing system of claim 13, wherein the embedding is generated by applying the plurality of attention layers to the first digital data representing the base ingredients and the second digital data representing the target sensory description, wherein the probability distribution of source ingredients is generated by the classification layer for the embedding.

\* \* \* \* \*